United States Patent [19]

Wagner et al.

[11] Patent Number: 5,565,490
[45] Date of Patent: Oct. 15, 1996

[54] P-HYDROXYANILINE DERIVATIVES, THEIR PREPARATION AND THEIR USE

[75] Inventors: Oliver Wagner, Bexbach; Karl Eicken, Wachenheim; Norbert Götz, Worms; Harald Rang, Altrip; Eberhard Ammermann, Heppenheim; Gisela Lorenz, Neustadt, all of Germany

[73] Assignee: BASF Aktiengesellschaft, Ludwigshafen, Germany

[21] Appl. No.: 339,235

[22] Filed: Nov. 10, 1994

[30] Foreign Application Priority Data

Nov. 11, 1993 [DE] Germany .......................... 43 38 469.2
May 26, 1994 [DE] Germany .......................... 44 18 379.8

[51] Int. Cl.$^6$ .......................... A01N 37/24; A01N 47/06; A01N 47/22; C07C 233/24
[52] U.S. Cl. .......................... 514/484; 514/488; 514/490; 514/512; 514/529; 514/530; 514/531; 514/534; 514/546; 558/271; 558/272; 560/1; 560/32; 560/109; 560/115; 560/122; 560/123; 560/124; 560/126; 560/128; 560/136; 560/142
[58] Field of Search .......................... 558/271, 272; 560/1, 32, 109, 115, 122, 123, 124, 126, 128, 136, 142; 514/484, 488, 490, 512, 529, 530, 531, 546, 534

[56] References Cited

U.S. PATENT DOCUMENTS

| | | | |
|---|---|---|---|
| 3,636,094 | 1/1972 | Yonan .................. | 260/518 R |
| 3,849,478 | 11/1974 | Payne et al. .......... | 260/479 C |
| 3,958,006 | 5/1976 | Payne, Jr. .............. | 424/300 |
| 4,578,498 | 3/1986 | Frickel et al. .......... | 560/8 |
| 5,059,623 | 10/1991 | Kruger et al. .......... | 514/613 |
| 5,371,271 | 12/1994 | Kruger et al. .......... | 560/136 |
| 5,376,681 | 12/1994 | Aono et al. ............ | 514/469 |

FOREIGN PATENT DOCUMENTS

| | | |
|---|---|---|
| 0293718 | 12/1988 | European Pat. Off. . |
| 0413666 | 2/1991 | European Pat. Off. . |
| 0416365 | 3/1991 | European Pat. Off. . |
| 0416359 | 3/1991 | European Pat. Off. . |
| 0483772 | 5/1992 | European Pat. Off. . |
| 0520252 | 12/1992 | European Pat. Off. . |
| 2354873 | 5/1974 | Germany . |

OTHER PUBLICATIONS

Nakajima et al., Chemical Abstracts, vol. 121, 108249u, 1994.
Database WPI, Derwent Publications Ltd., AN 94 040040, Jp-A-05 345 751, Dec. 27, 1993.

*Primary Examiner*—Richard L. Raymond
*Attorney, Agent, or Firm*—Oblon, Spivak, McClelland, Maier & Neustadt, P.C.

[57] ABSTRACT p-Hydroxyaniline derivatives of the formula I

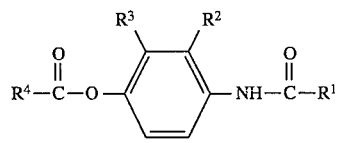

where the substituents have the following meanings:

$R^1$ is hydrogen, or unsubstituted or substituted alkyl;

$R^2$ and $R^3$ independently of one another are halogen, alkyl, haloalkyl, alkoxy or haloalkoxy;

$R^4$ is unsubstituted or substituted alkyl, alkenyl, cycloalkyl, cycloalkenyl or aryl, $OR^5$ or $NR^6R^7$, where $R^5$, $R^6$ are unsubstituted or substituted alkyl, alkenyl, cycloalkyl, cycloalkenyl or aryl, and $R^7$ is hydrogen or alkyl, and their salts, processes for their preparation, compositions containing them and their use for controlling harmful fungi or pests, and also compounds of the formula VI

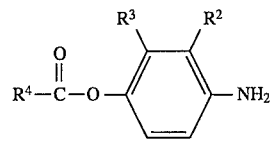

and their salts, processes for their preparation, compositions containing them and their use as intermediates and for controlling pests are described.

6 Claims, No Drawings

P-HYDROXYANILINE DERIVATIVES, THEIR PREPARATION AND THEIR USE

The present invention relates to p-hydroxyaniline derivatives of the formula I

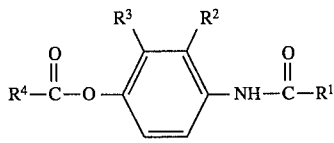

where the substituents have the following meanings:

$R^1$ is hydrogen, $C_1$–$C_8$-alkyl which can be partly or completely halogenated and/or which can carry one or two of the following radicals: $C_1$–$C_4$-alkoxy, $C_1$–$C_4$-haloalkoxy, $C_1$–$C_4$-alkylthio, $C_3$–$C_7$-cycloalkyl or $C_5$–$C_7$-cycloalkenyl, the cyclic radicals in turn being able to carry one to three halogen atoms, $C_1$–$C_3$-alkyl groups and/or $C_1$–$C_3$-alkoxy groups and aryl, which can be partly or completely halogenated and/or can carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

$R^2$ and $R^3$ independently of one another are halogen, $C_1$–$C_4$-alkyl, $C_1$–$C_4$-haloalkyl, $C_1$–$C_4$-alkoxy or $C_1$–$C_4$-haloalkoxy;

$R^4$ is $C_1$–$C_6$-alkyl or $C_2$–$C_6$-alkenyl, it being possible for these groups to be partly or completely halogenated and/or to carry one of the following radicals: $C_1$–$C_4$-alkoxy, $C_1$–$C_4$-haloalkoxy, $C_1$–$C_4$-alkylthio, $C_3$–$C_7$-cycloalkyl, $C_5$–$C_7$-cycloalkenyl or aryl, the aromatic radicals in turn being able to carry one to three of the following groups: nitro, cyano, halogen, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

$C_3$–$C_7$-cycloalkyl or $C_5$–$C_7$-cycloalkenyl, these groups being able to carry one to three of the following radicals: halogen, $C_1$–$C_4$-alkyl, $C_1$–$C_4$-haloalkyl and $C_1$–$C_4$-alkoxy;

aryl, which can be partly or completely halogenated and/or can carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

$OR^5$ or $NR^6R^7$, where $R^5$ is $C_1$–$C_6$-alkyl or $C_2$–$C_6$-alkenyl, it being possible for these groups to be partly or completely halogenated and/or to carry one of the following radicals: $C_1$–$C_4$-alkoxy, $C_1$–$C_4$-haloalkoxy, $C_1$–$C_4$-alkylthio, $C_3$–$C_7$-cycloalkyl, $C_5$–$C_7$-cycloalkenyl or aryl, it being possible for the aromatic radicals in turn to carry one to three of the following groups: nitro, cyano, halogen, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

is $C_3$–$C_7$-cycloalkyl or $C_5$–$C_7$-cycloalkenyl, it being possible for these groups to carry one to three of the following radicals: halogen, $C_1$–$C_4$-alkyl, $C_1$–$C_4$-haloalkyl and $C_1$–$C_4$-alkoxy;

or is aryl, which can be partly or completely halogenated and/or can carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

$R^6$ is $C_1$–$C_6$-alkyl or $C_2$–$C_6$-alkenyl, it being possible for these groups to be partly or completely halogenated and/or to carry one of the following radicals: $C_1$–$C_4$-alkylthio, $C_3$–$C_7$-cycloalkyl, $C_5$–$C_7$-cycloalkenyl or aryl, it being possible for the aromatic radicals in turn to carry one to three of the following groups: nitro, cyano, halogen, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

is $C_3$–$C_7$-cycloalkyl or $C_5$–$C_7$-cycloalkenyl, it being possible for these groups to carry one to three of the following radicals: halogen, $C_1$–$C_4$-alkyl, $C_1$–$C_4$-haloalkyl and $C_1$–$C_4$-alkoxy;

or is aryl, which can be partly or completely halogenated and/or can carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio; and $R^7$ is hydrogen or $C_1$–$C_6$-alkyl, where $R^1$, $R^2$, $R^3$ and $R^4$ are not simultaneously methyl, and their salts.

The invention additionally relates to processes for preparing the compounds I, compositions containing them, their use for preparing compositions of this type, and their use for controlling harmful fungi or pests.

The invention furthermore relates to compounds of the general formula VI

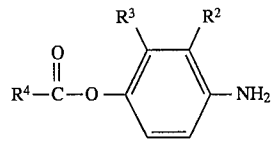

and their salts.

The invention additionally relates to a process for preparing specific compounds VI, the use of the compounds VI as intermediates, and compositions containing them and their use for controlling pests.

Alkylcarboxanilides having insecticidal or fungicidal action are known from the literature (U.S. Pat. No. 3,849,478, U.S. Pat. No. 3,958,006, EP-A 293 718 and JP-A 345 751/93).

The compound of the formula I, where $R^1$, $R^2$, $R^3$ and $R^4$ are methyl, is additionally described as an intermediate for preparing pharmaceuticals in EP-A 483 772.

It is an object of the present invention to provide novel compounds having improved action against a wider spectrum of harmful fungi.

We have now found that this object is achieved by the compounds I defined at the outset.

We have additionally found processes for preparing the compounds I, compositions containing them, their use for preparing compositions of this type, and their use for controlling harmful fungi.

We have furthermore found a process for preparing specific compounds VI, the use of the compounds VI as intermediates, and compositions containing them and their use for controlling pests.

In general, the compounds I can be prepared in a manner known per se starting from the corresponding p-hydroxyanilines by esterification of the phenolic OH group and amidation of the $NH_2$ group according to the following reaction scheme.

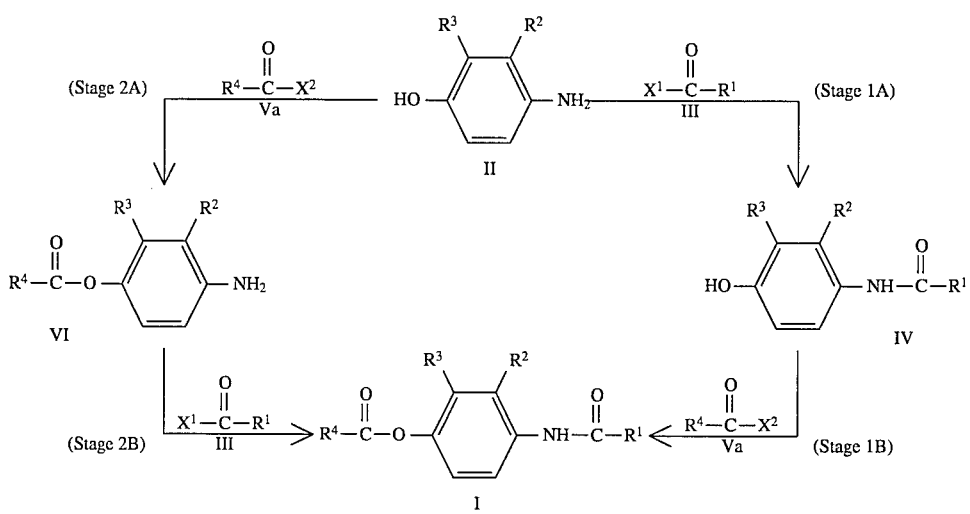

The individual reaction steps are customarily carried out as follows:

Stage 1A: Preparation of the carboxanilides IV

The carboxanilides of the formula IV are obtained by reacting a p-hydroxyaniline of the formula II with a carbonyl derivative of the formula III in a manner known per se (DE-A 32 02 100 (EP-A 339 418)) in an inert organic solvent in the presence of a base.

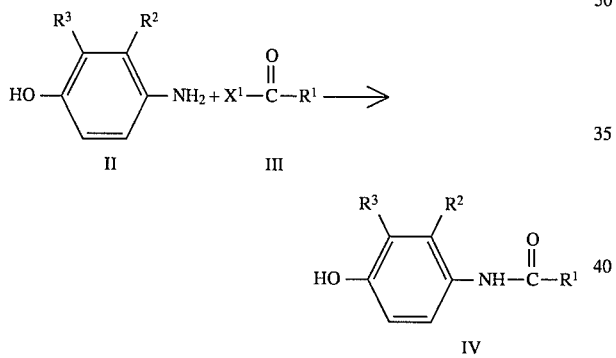

The variable $X^1$ in the formula III is halogen such as in particular, chlorine, bromine or iodine, or a leaving group which can be used in acylation reactions, eg. $R^1$—CO—O.

This reaction is customarily carried out at from $-70°$ C. to $140°$ C., preferably $0°$ C. to $110°$ C.

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, and also dimethyl sulfoxide and dimethylformamide, particularly preferably dioxane, tetrahydrofuran and dimethylformamide.

Mixtures of the solvents mentioned can also be used.

Suitable bases generally are inorganic compounds such as alkali metal and alkaline earth metal hydroxides such as lithium hydroxide, sodium hydroxide, potassium hydroxide and calcium hydroxide, alkali metal and alkaline earth metal oxides such as lithium oxide, sodium oxide, calcium oxide and magnesium oxide, alkali metal amides such as lithium amide, sodium amide and potassium amide, alkali metal and alkaline earth metal carbonates such as lithium carbonate and calcium carbonate as well as alkali metal hydrogencarbonates such as sodium hydrogencarbonate, alkali metal and alkaline earth metal alkoxides such as, sodium methoxide, sodium ethoxide, potassium ethoxide, potassium tert-butoxide and dimethoxymagnesium, additionally organic bases, eg. tertiary amines such as trimethylamine, triethylamine, triisopropylethylamine and N-methylpiperidine, pyridine, substituted pyridines such as collidine, lutidine and 4-dimethylaminopyridine, and bicyclic amines.

Alkali metal carbonates, alkali metal alkoxides and tertiary amines are particularly preferred.

In general, the bases are employed in equimolar amounts, but they can also be used in an excess or, if appropriate, as a solvent.

In general, the starting materials are reacted with one another in equimolar amounts. It may be advantageous for the yield to employ III in an excess or deficit based on II.

The starting substances II and III required for the reaction are known from the literature (II: J. Chem. Soc. Pt I, 1, (1973) 1; Houben-Weyl, Vol. 10/1, p. 1140ff; ibid. Vol. 6/1c, pp. 85–101; III: Houben-Weyl, E5, Part 1, p. 587; Can. J. Chem. 71, (1993) pp. 1099–1105) or can be prepared according to the cited references.

Stage 1B: Preparation of the p-hydroxyaniline derivatives I from the carboxanilides IV The p-hydroxyaniline derivatives I are obtained by reacting a carboxanilide of the formula IV with a carbonyl derivative of the formula Va.

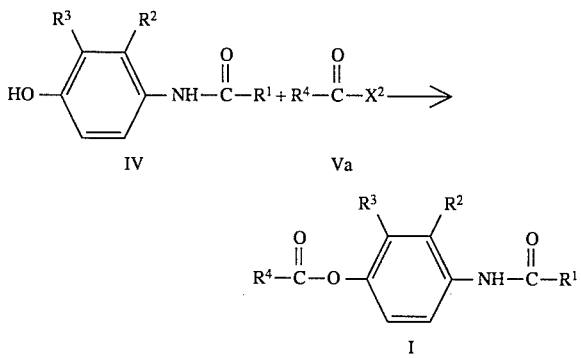

The variable $X^2$ in the formula Va is halogen such as, in particular, chlorine, bromine or iodine.

This reaction is customarily carried out at from −70° C. to 140° C., preferably 0° C. to 110° C.

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, and also dimethyl sulfoxide and dimethylformamide, particularly preferably dichloromethane, tetrahydrofuran, acetone and dimethylformamide.

Mixtures of the solvents mentioned can also be used.

Suitable bases generally are inorganic compounds such as alkali metal and alkaline earth metal hydroxides such as lithium hydroxide, sodium hydroxide, potassium hydroxide and calcium hydroxide, alkali metal and alkaline earth metal oxides such as lithium oxide, sodium oxide, calcium oxide and magnesium oxide, alkali metal and alkaline earth metal hydrides such as lithium hydride, sodium hydride, potassium hydride and calcium hydride, alkali metal amides such as lithium amide, sodium amide and potassium amide, alkali metal and alkaline earth metal carbonates such as lithium carbonate and calcium carbonate as well as alkali metal hydrogencarbonates such as sodium hydrogencarbonate, alkali metal and alkaline earth metal alkoxides such as sodium methoxide, sodium ethoxide, potassium ethoxide, potassium tert-butoxide and dimethoxymagnesium, additionally organic bases, eg. tertiary amines such as trimethylamine, triethylamine, triisopropylethylamine and N-methylpiperidine, pyridine, substituted pyridines such as collidine, lutidine and 4-dimethylaminopyridine, and bicyclic amines.

Alkali metal carbonates, alkali metal alkoxides and tertiary amines are particularly preferred.

In general, the bases are employed in equimolar amounts, but they can also be used in an excess or, if appropriate, as a solvent.

In general, the compounds IV and Va are reacted with one another in equimolar amounts. It may be advantageous for the yield to employ Va in an excess or deficit based on IV.

The starting substances Va or Vb required for the reaction are known from the literature (Houben-Weyl, E4, p. 9; Houben-Weyl, E5, part 1, p. 587; Houben-Weyl, E4, p. 738) or can be prepared according to the cited references.

Compounds I in which $R^4$ is a group $NHR^6$ are particularly preferably obtained by reacting a carboxamide of the formula IV with an isocyanate of the formula Vb in a manner known per se (Houben-Weyl, E4, p. 768).

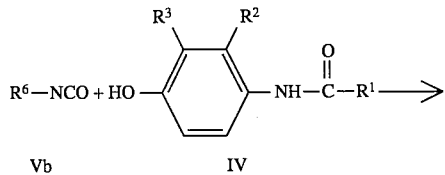

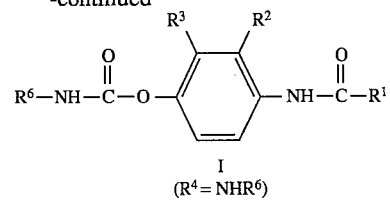
($R^4 = NHR^6$)

This reaction is customarily carried out at from −20° C. to 140° C., preferably −5° C. to 50° C.

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, and also dimethyl sulfoxide and dimethylformamide, particularly preferably tetrahydrofuran, methylene chloride and dimethylformamide.

Mixtures of the solvents mentioned can also be used.

In general, the compounds IV and Vb are reacted with one another in equimolar amounts. It may be advantageous for the yield to employ one of the compounds in an excess or deficit based on the other.

Stage 2A: Preparation of the compounds VI

The compounds of the formula VI are obtained by reacting a p-hydroxyaniline of the formula II or a corresponding phenoxide with a carbonyl derivative of the formula Va in a manner known per se (Houben-Weyl, E4, p. 68) in an inert organic solvent in the presence of a base.

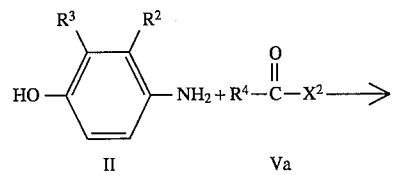

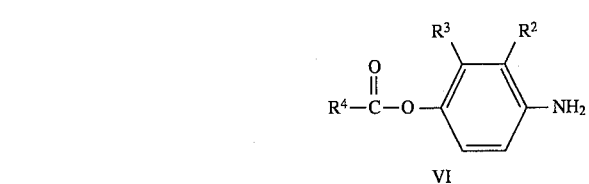

The variable $X^2$ in the formula Va is halogen such as, in particular, chlorine, bromine or iodine.

This reaction is customarily carried out at from −70° C. to 140° C., preferably 0° C. to 110° C.

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, and also dimethyl sulfoxide and dimethylformamide, particularly preferably tetrahydrofuran, acetone and dimethylformamide.

Mixtures of the solvents mentioned can also be used.

Suitable bases generally are inorganic compounds such as alkali metal and alkaline earth metal hydroxides such as lithium hydroxide, sodium hydroxide, potassium hydroxide and calcium hydroxide, alkali metal and alkaline earth metal oxides such as lithium oxide, sodium oxide, calcium oxide and magnesium oxide, alkali metal and alkaline earth metal hydrides such as lithium hydride, sodium hydride, potassium hydride and calcium hydride, alkali metal amides such as lithium amide, sodium amide and potassium amide, alkali metal and alkaline earth metal carbonates such as lithium carbonate and calcium carbonate as well as alkali metal hydrogencarbonates such as sodium hydrogencarbonate, alkali metal and alkaline earth metal alkoxides such as sodium methoxide, sodium ethoxide, potassium ethoxide, potassium tert-butoxide and dimethoxymagnesium, additionally organic bases, eg. tertiary amines such as trimethylamine, triethylamine, triisopropylethylamine and N-methylpiperidine, pyridine, substituted pyridines such as collidine, lutidine and 4-dimethylaminopyridine, and bicyclic amines.

Alkali metal carbonates, alkali metal hydrides and alkali metal alkoxides are particularly preferred.

In general, the bases are employed in equimolar amounts, but they can also be used in an excess or, if appropriate, as a solvent.

In general, the compounds II and Va are reacted with one another in equimolar amounts. It may be advantageous for the yield to employ Va in an excess or deficit based on II.

The compounds VI in which $R^4$ is a group $NHR^7$ are particularly preferably obtained by reacting a p-hydroxyaniline of the formula II or the corresponding phenoxide with an isocyanate of the formula Vb in a manner known per se (Houben-Weyl, E4, p. 768).

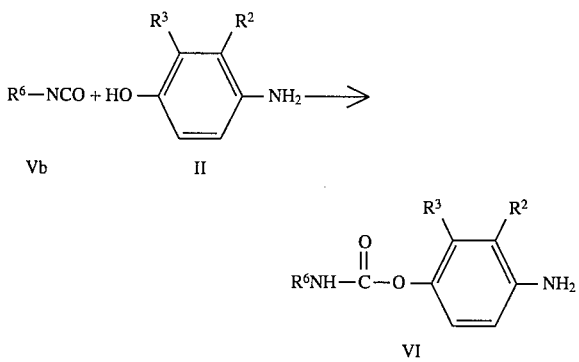

This reaction is customarily carried out at from −20° C. to 140° C., preferably −5° C. to 50° C.

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, and also dimethyl sulfoxide and dimethylformamide, particularly preferably tetrahydrofuran, methylene chloride, dimethylformamide and toluene.

Mixtures of the solvents mentioned can also be used.

In general, the compounds II and Vb are reacted with one another in equimolar amounts. It may be advantageous for the yield to employ one of the compounds in an excess or deficit based on the other.

Stage 2B: Preparation of the p-hydroxyaniline derivatives I from the compounds VI The p-hydroxyaniline derivatives I are obtained by reacting a compound of the formula VI with a carbonyl derivative of the formula III.

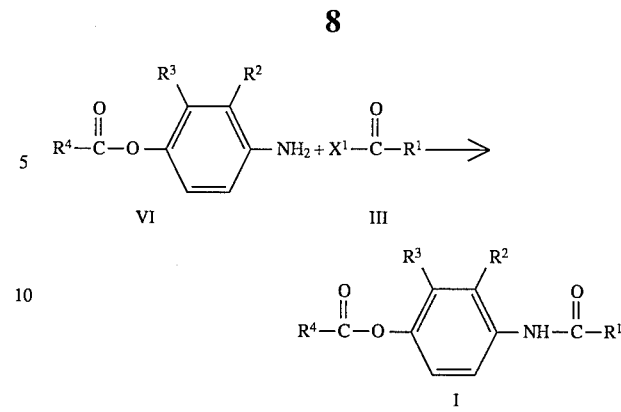

The variable $X^1$ in the formula III is halogen such as, in particular, chlorine, bromine or iodine, or a leaving group which can be used in acylation reactions, eg. as mentioned above in Stage 1A.

This reaction is customarily carried out at from −70° C. to 140° C., preferably 0° C. to 110° C.

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, and also dimethyl sulfoxide and dimethylformamide, particularly preferably toluene, tetrahydrofuran, acetone and dimethyl sulfoxide.

Mixtures of the solvents mentioned can also be used.

Suitable bases generally are inorganic compounds such as alkali metal and alkaline earth metal hydroxides such as lithium hydroxide, sodium hydroxide, potassium hydroxide and calcium hydroxide, alkali metal and alkaline earth metal oxides such as lithium oxide, sodium oxide, calcium oxide and magnesium oxide, alkali metal and alkaline earth metal hydrides such as lithium hydride, sodium hydride, potassium hydride and calcium hydride, alkali metal amides such as lithium amide, sodium amide and potassium amide, alkali metal and alkaline earth metal carbonates such as lithium carbonate and calcium carbonate as well as alkali metal hydrogencarbonates such as sodium hydrogencarbonate, alkali metal and alkaline earth metal alkoxides such as sodium methoxide, sodium ethoxide, potassium ethoxide, potassium tert-butoxide and dimethoxymagnesium, additionally organic bases, eg. tertiary amines such as trimethylamine, triethylamine, triisopropylethylamine and n-methylpiperidine, pyridine, substituted pyridines such as collidine, lutidine and 4-dimethylaminopyridine, and bicyclic amines.

Tertiary amines, alkali metal carbonates and alkali metal alkoxides are particularly preferred.

In general, the bases are employed in equimolar amounts, but they can also be used in an excess or, if appropriate, as a solvent.

In general, the compounds IV and Va are reacted with one another in equimolar amounts. It may be advantageous for the yield to employ Va in an excess or deficit based on IV.

The reaction mixtures are worked up in a customary manner, eg. by mixing with water, separating the phases and, if appropriate, chromatographically purifying the crude products. The intermediates and final products are in some cases obtained in the form of colorless or slightly brownish, viscous oils, which are freed from volatile components under reduced pressure and at moderately elevated temperature or purified. If the intermediates and final products are obtained as solids, purification can also be carried out by recrystallizing or digesting.

The compounds I can contain one or more centers of asymmetry and are obtained by the processes described in the form of enantiomer or diastereomer mixtures. The quantitative ratios here can be different depending on the groups. These mixtures may, if appropriate, be separated by customary methods. The compounds I can be used either as pure isomers or as isomer mixtures.

Because of the basic character of the NH or $NH_2$ group, the compound I or VI is able to form salts or adducts with inorganic or organic acids or with metal ions.

Examples of inorganic acids are hydrohalic acids such as hydrofluoric acid, hydrochloric acid, hydrobromic acid and hydriodic acid, sulfuric acid, phosphoric acid and nitric acid.

Suitable organic acids are, for example, formic acid, carbonic acid and alkanoic acids such as acetic acid, trifluoroacetic acid, trichloroacetic acid and propionic acid, and glycolic acid, thiocyanic acid, lactic acid, succinic acid, citric acid, benzoic acid, cinnamic acid, oxalic acid, alkanesulfonic acids, (sulfonic acids containing straight-chain or branched alkyl radicals having 1 to 20 carbon atoms), arylsulfonic acids or -disulfonic acids (aromatic radicals such as phenyl and naphthyl which carry one or two sulfo groups), alkanephosphonic acids (phosphonic acids containing straight-chain or branched alkyl radicals having 1 to 20 carbon atoms), arylphosphonic acids or -diphosphonic acids (aromatic radicals such as phenyl and naphthyl which carry one or two phosphonic acid radicals), where the alkyl or aryl radicals can carry further substituents, eg. p-toluenesulfonic acid, salicylic acid, p-aminosalicylic acid, 2-phenoxybenzoic acid, 2-acetoxybenzoic acid etc.

Suitable metal ions are, in particular, the ions of elements of the second main group, in particular calcium and magnesium, the third and fourth main group, in particular aluminum, tin and lead, and also of the first to eighth subgroup, in particular chromium, manganese, iron, cobalt, nickel, copper, zinc and others. The metal ions of the elements of the subgroups of the fourth period are particularly preferred. The metals can be present here in the various valencies befitting them.

The compounds prepared and used in the processes described above, of the formula VI

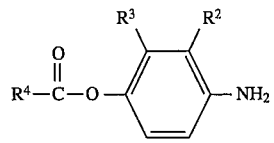

where the substituents $R^2$, $R^3$ and $R^4$ have the meanings given at the outset, and their salts are novel.

In the definitions of the compounds I and VI given at the outset, collective terms were used which are generally representative of the following substituents:

Halogen: fluorine, chlorine, bromine and iodine;

alkyl: straight-chain or branched alkyl groups having 1 to 3, 4, 6 or 8 carbon atoms, eg. $C_1$–$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

haloalkyl or partly or completely halogenated alkyl: straight-chain or branched alkyl groups having 1 to 4, 6 or 8 carbon atoms as mentioned above, where the hydrogen atoms in these groups can be partly or completely replaced by halogen atoms as mentioned above, eg. $C_1$–$C_2$-haloalkyl such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

alkoxy: straight-chain or branched alkoxy groups having 1 to 3 or 4 carbon atoms, such as methoxy, ethoxy, propoxy, 1-methylethoxy, butoxy, 1-methylpropoxy, 2-methylpropoxy and 1,1-dimethylethoxy;

haloalkoxy: straight-chain or branched partly or completely halogenated alkyl groups having 1 to 4 carbon atoms as mentioned above, where these groups are bonded to the structure via an oxygen atom (—O—);

alkylthio: straight-chain or branched alkyl groups having 1 to 4 carbon atoms as mentioned above, which are bonded to the structure via a sulfur atom (—S—);

alkenyl: straight-chain or branched alkenyl groups having 2 to 6 carbon atoms and a double bond in any desired position, eg. ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl- 2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

cycloalkyl: monocyclic alkyl groups having 3 to 7 carbon ring members: cyclopropyl, cyclobutyl, cyclopentyl, cyclohexyl, and cycloheptyl;

cycloalkenyl: monocyclic alkenyl groups having 5 to 7 carbon ring members and one or two double bonds: 1-cyclopentenyl, 2-cyclopentenyl, 3-cyclopentenyl, 1,3-cyclopentadienyl, 1,4-cyclopentadienyl, 1-cyclohexenyl, 2-cyclohexenyl, 3-cyclohexenyl, 1,3-cyclohexadienyl, 1,4-cyclohexadienyl, 1,5-cyclohexadienyl, 2,4-cyclohexadienyl, 1-cycloheptenyl, 2-cycloheptenyl, 3-cycloheptenyl, 4-cycloheptenyl, 1,3-cycloheptadienyl, 1,4-cycloheptadienyl, 1,5-cycloheptadienyl, 1,6-cycloheptadienyl, 2,4-cycloheptadienyl, 2,5-cycloheptadienyl, 2,6-cycloheptadienyl and 3,5-cycloheptadienyl;

aryl: phenyl or naphthyl.

The statement partly or completely halogenated is intended to express that in the groups characterized in this way the hydrogen atoms can be partly or completely replaced by identical or different halogen atoms as mentioned above.

With respect to their biological action against harmful fungi, compounds of the formula I are preferred in which $R^1$ is an alkyl group which is branched or substituted in the 1-position, preferred substituents being: halogen, $C_1$–$C_4$-alkoxy and aryl which can be partly or completely halogenated and/or can carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio.

Compounds are additionally preferred in which $R^2$ is halogen, alkyl or alkoxy.

In addition, compounds I are preferred in which $R^2$ is alkyl, in particular methyl.

Moreover, compounds I are preferred in which $R^2$ is fluorine or chlorine.

Compounds are additionally preferred in which $R^3$ is alkyl, haloalkyl, alkoxy or haloalkoxy.

In addition, compounds I are preferred in which $R^3$ is halogen, alkyl, haloalkyl or haloalkoxy.

Moreover, compounds I are preferred in which $R^3$ is fluorine, chlorine, methyl or trifluoromethyl.

Other preferred compounds I are those in which $R^4$ is the following groups:

$C_1$–$C_6$-alkyl or $C_2$–$C_6$-alkenyl, where these groups can be partly or completely halogenated and/or can carry one of the following radicals: $C_1$–$C_4$-alkoxy, $C_1$–$C_4$-haloalkoxy, $C_1$–$C_4$-alkylthio, $C_3$–$C_7$-cycloalkyl, $C_5$–$C_7$-cycloalkenyl or aryl, where the aromatic radicals in turn can carry one to three of the following groups: nitro, cyano, halogen, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

$C_3$–$C_7$-cycloalkyl or $C_5$–$C_7$-cycloalkenyl, where these groups can carry one to three of the following radicals: halogen, $C_1$–$C_4$-alkyl, $C_1$–$C_4$-haloalkyl and $C_1$–$C_4$-alkoxy;

aryl, which can be partly or completely halogenated and can carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio.

In addition, compounds I are preferred in which $R^4$ is $OR^5$ or $NR^6R^7$, where $R^5$ is $C_1$–$C_6$-alkyl or $C_2$–$C_6$-alkenyl, where these groups can be partly or completely halogenated and/or can carry one of the following radicals: $C_1$–$C_4$-alkoxy, $C_1$–$C_4$-haloalkoxy, $C_1$–$C_4$-alkylthio, $C_3$–$C_7$-cycloalkyl, $C_5$–$C_7$-cycloalkenyl or aryl, where the aromatic radicals in turn can carry one to three of the following groups: nitro, cyano, halogen, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

is $C_3$–$C_7$-cycloalkyl or $C_5$–$C_7$-cycloalkenyl where these groups can carry one to three of the following radicals: halogen, $C_1$–$C_4$-alkyl, $C_1$–$C_4$-haloalkyl and $C_1$–$C_4$-alkoxy;

or is aryl, which can be partly or completely halogenated and/or can carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

$R^6$ is $C_1$–$C_6$-alkyl or $C_2$–$C_6$-alkenyl, where these groups can be partly or completely halogenated and/or can carry one of the following radicals: $C_1$–$C_4$-alkylthio, $C_3$–$C_7$-cycloalkyl, $C_5$–$C_7$-cycloalkenyl or aryl, where the aromatic radicals in turn can carry one to three of the following groups: nitro, cyano, halogen, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

is $C_3$–$C_7$-cycloalkyl or $C_5$–$C_7$-cycloalkenyl, where these groups can carry one to three of the following radicals: halogen, $C_1$–$C_4$-alkyl, $C_1$–$C_4$-haloalkyl and $C_1$–$C_4$-alkoxy;

or is aryl, which can be partly or completely halogenated and/or can carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio; and $R^7$ is hydrogen or $C_1$–$C_6$-alkyl.

Particularly preferred compounds I are those in which $R^2$ and $R^3$ independently of one another are halogen, $C_1$–$C_4$-alkyl, $C_1$–$C_4$-haloalkyl, $C_1$–$C_4$-alkoxy and $C_1$–$C_4$-haloalkoxy and $R^4$ is $C_1$–$C_6$-alkyl or $C_2$–$C_6$-alkenyl, where these groups can be partly or completely halogenated and/or can carry one of the following radicals: $C_1$–$C_4$-alkoxy, $C_1$–$C_4$-haloalkoxy, $C_1$–$C_4$-alkylthio, $C_3$–$C_7$-cycloalkyl, $C_5$–$C_7$-cycloalkenyl or aryl, where the aromatic radicals in turn can carry one to three of the following groups: nitro, cyano, halogen, $C_1$–$C_4$-alkyl, $C_1$–$C_4$-haloalkyl, $C_1$–$C_4$-alkoxy, $C_1$–$C_4$-haloalkoxy and $C_1$–$C_4$alkylthio; or $R^4$ is $C_3$–$C_7$-cycloalkyl or $C_5$–$C_7$-cycloalkenyl, where these groups can carry one to three of the following radicals: halogen, $C_1$–$C_4$-alkyl, $C_1$–$C_4$-haloalkyl and $C_1$–$C_4$-alkoxy; or $R^4$ is aryl, which can be partly or completely halogenated and can carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio.

In addition, compounds I are also preferred in which the radicals $R^2$, $R^3$ and $R^4$ have the following meanings:

$R^2$ is halogen, $C_1$–$C_4$-alkyl, $C_1$–$C_4$-haloalkyl, $C_1$–$C_4$-alkoxy and $C_1$–$C_4$-haloalkoxy;

$R^3$ is $C_1$–$C_4$-alkyl, $C_1$–$C_4$-haloalkyl, $C_1$–$C_4$-alkoxy and $C_1$–$C_4$-haloalkoxy;

$R^4$ is $OR^5$ or $NR^6R^7$ where $R^5$ is $C_1$–$C_6$-alkyl or $C_2$–$C_6$-alkenyl, where these groups can be partly or completely halogenated and/or can carry one of the following radicals: $C_1$–$C_4$-alkoxy, $C_1$–$C_4$-haloalkoxy, $C_1$–$C_4$-alkylthio, $C_3$–$C_7$-cycloalkyl, $C_5$–$C_7$-cycloalkenyl or aryl, where the aromatic radicals in turn can carry one to three of the following groups: nitro, cyano, halogen, $C_1$–$C_4$-alkyl, $C_1$–$C_4$-haloalkyl, $C_1$–$C_4$-alkoxy, $C_1$–$C_4$-haloalkoxy and $C_1$–$C_4$alkylthio;

is $C_3$–$C_7$-cycloalkyl or $C_5$–$C_7$-cycloalkenyl, where these groups can carry one to three of the following radicals: halogen, $C_1$–$C_4$-alkyl, $C_1$–$C_4$-haloalkyl and $C_1$–$C_4$-alkoxy;

or is aryl, which can be partly or completely halogenated and/or can carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

$R^6$ is $C_1$–$C_6$-alkyl or $C_2$–$C_6$-alkenyl, where these groups can be partly or completely halogenated and/or can carry one of the following radicals: $C_1$–$C_4$-alkylthio, $C_3$–$C_7$-cycloalkyl, $C_5$–$C_7$-cycloalkenyl or aryl, where the aromatic radicals in turn can carry one to three of the following groups: nitro, cyano, halogen, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

is $C_3$–$C_7$-cycloalkyl or $C_5$–$C_7$-cycloalkenyl where these groups can carry one to three of the following radicals: halogen, $C_1$–$C_4$-alkyl, $C_1$–$C_4$-haloalkyl and $C_1$–$C_4$-alkoxy;

or is aryl, which can be partly or completely halogenated and/or can carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio; and $R^7$ is hydrogen or $C_1$–$C_6$-alkyl.

In particular, those compounds I are also preferred in which $R^1$ is 1,1-dimethylethyl, 1,1-dimethylpropyl, 1-methyl-1-ethylpropyl, 2-chloro-1,1-dimethylethyl and 2-fluoro-1,1-dimethylethyl.

Furthermore, those compounds I are preferred in which $R^4$ is $OR^5$, where $R^5$ is one of the following groups: methyl, ethyl, propyl, isopropyl, butyl, isobutyl, propenyl or benzyl where the benzyl radical can carry one to five halogen atoms and/or one to three of the following groups: $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio.

In addition, those compounds I are preferred in which $R^4$ is $NR^6R^7$, where $R^7$ is hydrogen or methyl and $R^6$ is one of the following groups: methyl, ethyl, propyl, isopropyl, butyl, isobutyl, propenyl or benzyl, where the benzyl radical can carry one to five halogen atoms and/or one to three of the following groups: $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio.

With respect to their biological action against pests, compounds of the general formula I are preferred in which the radicals have the following meanings, per se or in combination:

$R^1$ is hydrogen or $C_1C_4$-alkyl, especially hydrogen or methyl;

$R^2$ is halogen, especially fluorine and in particular chlorine;

$R^3$ is halogen, $C_1$–$C_4$-alkyl or $C_1$–$C_4$-haloalkyl, especially halogen and in particular chlorine or fluorine;

$R^4$ is $NR^5R^6$, especially with $R^5$ being $C_1$–$C_4$-alkyl, in particular methyl, and especially with $R^6$ being hydrogen.

With respect to their biological action against pests, compounds of the general formula VI are also preferred in which the radicals have the following meanings, per se or in combination:

$R^2$ is halogen, especially fluorine and in particular chlorine;

$R^3$ is halogen, $C_1$–$C_4$-alkyl or $C_1$–$C_4$-haloalkyl, especially halogen, in particular fluorine and very particularly preferably chlorine;

$R^4$ is $NR^6R^7$, especially with $R^6$ being $C_1$–$C_4$-alkyl, in particular methyl, and especially with $R^7$ being hydrogen.

In particular, with respect to their use for controlling harmful fungi or pests, the compounds I compiled in the following tables are preferred.

Table 1

Compounds of the general formula I.1, in which the combination of the substituents $R^2$, $R^3$ and $R^4$ for one compound in each case corresponds to one line of Table A

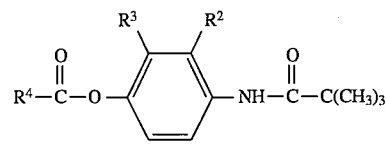

Table 2

Compounds of the general formula I.2, in which the combination of the substituents $R^2$, $R^3$ and $R^4$ for one compound in each case corresponds to one line of Table A

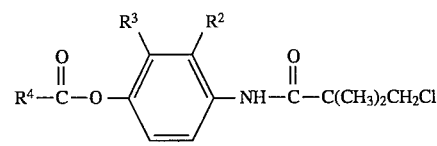

Table 3

Compounds of the general formula I.3, in which the combination of the substituents $R^2$, $R^3$ and R4 for one compound in each case corresponds to one line of Table A

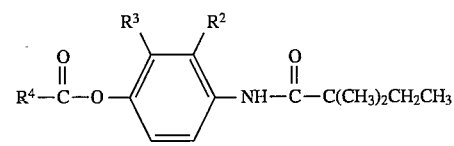

Table 4

Compounds of the general formula I.4, in which the combination of the substituents $R^2$, $R^3$ and $R^4$ for one compound in each case corresponds to one line of Table A

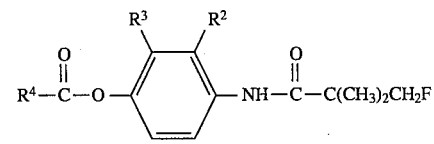

Table 5

Compounds of the general formula I.5, in which the combination of the substituents $R^2$, $R^3$ and $R^4$ for one compound in each case corresponds to one line of Table A

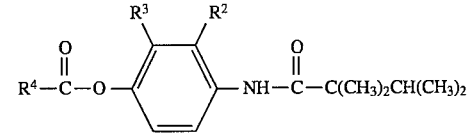

Table 6

Compounds of the general formula I.6, in which the combination of the substituents $R^2$, $R^3$ and $R^4$ for one compound in each case corresponds to one line of Table A

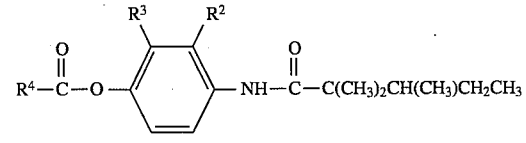

Table 7

Compounds of the general formula I.7, in which the combination of the substituents $R^2$, $R^3$ and $R^4$ for one compound in each case corresponds to one line of Table A

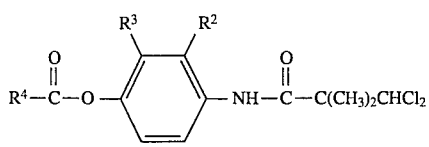

I.7

Table 8

Compounds of the general formula I.8, in which the combination of the substituents $R^2$, $R^3$ and $R^4$ for one compound in each case corresponds to one line of Table A

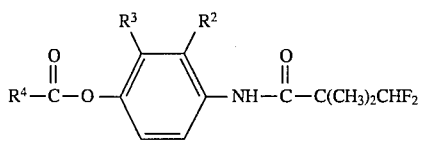

I.8

Table 9

Compounds of the general formula I.9, in which the combination of the substituents $R^2$, $R^3$ and $R^4$ for one compound in each case corresponds to one line of Table A

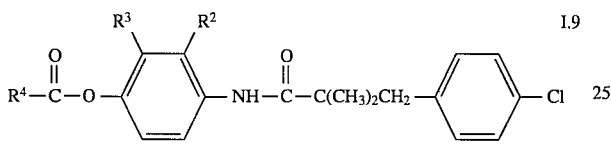

I.9

Table 10

Compounds of the general formula I.10, in which the combination of the substituents $R^2$, $R^3$ and $R^4$ for one compound in each case corresponds to one line of Table A

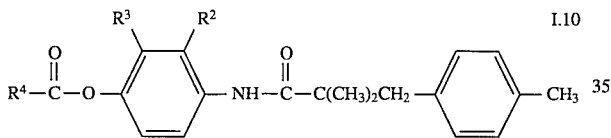

I.10

With respect to their use as intermediates for preparing the compounds I or for controlling pests, the compounds of the formula VI are preferred in which the combination of the radicals $R^2$, $R^3$ and $R^4$ for one compound in each case corresponds to one line of Table A.

TABLE A

| No. | $R^2$ | $R^3$ | $R^4$ |
|---|---|---|---|
| 1 | Cl | Cl | OCH₃ |
| 2 | Cl | Cl | OCH₂CH₃ |
| 3 | Cl | Cl | O(CH₂)₂CH₃ |
| 4 | Cl | Cl | OCH(CH₃)₂ |
| 5 | Cl | Cl | O(CH₂)₃CH₃ |
| 6 | Cl | Cl | OCH₂CH(CH₃)₂ |
| 7 | Cl | Cl | OCH(CH₃)CH₂CH₃ |
| 8 | Cl | Cl | OC(CH₃)₃ |
| 9 | Cl | Cl | O(CH₂)₄CH₃ |
| 10 | Cl | Cl | O(CH₂)₂CH(CH₃)₂ |
| 11 | Cl | Cl | OCH₂C(CH₃)₃ |
| 12 | Cl | Cl | OC(CH₃)₂CH₂CH₃ |
| 13 | Cl | Cl | O(CH₂)₅CH₃ |
| 14 | Cl | Cl | OCH₂CH=CH₂ |
| 15 | Cl | Cl | OCH₂CH=CHCH₃ |
| 16 | Cl | Cl | OC₆H₅ |
| 17 | Cl | Cl | O—(4-CH₃—C₆H₄) |
| 18 | Cl | Cl | O—(4-Cl—C₆H₄) |
| 19 | Cl | Cl | O—(2,4-Cl₂—C₆H₃) |
| 20 | Cl | Cl | O—(4-C(CH₃)₃—C₆H₄) |
| 21 | Cl | Cl | OCH₂C₆H₅ |
| 22 | Cl | Cl | OCH₂—(4-CH₃—C₆H₄) |
| 23 | Cl | Cl | OCH₂—(4-Cl—C₆H₄) |
| 24 | Cl | Cl | OCH₂—(4-F—C₆H₄) |
| 25 | Cl | Cl | OCH₂—(2,4-Cl₂—C₆H₃) |
| 26 | Cl | Cl | OCH₂—(4-C(CH₃)₃—C₆H₄) |
| 27 | Cl | Cl | OCH₂—(2-CH₃—C₆H₄) |
| 28 | Cl | Cl | OCH₂—(2-Cl—C₆H₄) |
| 29 | Cl | Cl | OCH₂—(2-F—C₆H₄) |
| 30 | Cl | Cl | OCH₂—(3-CH₃—C₆H₄) |
| 31 | Cl | Cl | OCH₂—(3-Cl—C₆H₄) |
| 32 | Cl | Cl | OCH₂—(3-F—C₆H₄) |
| 33 | Cl | Cl | NHCH₃ |
| 34 | Cl | Cl | NHCH₂CH₃ |
| 35 | Cl | Cl | NH(CH₂)₂CH₃ |
| 36 | Cl | Cl | NHCH(CH₃)₂ |
| 37 | Cl | Cl | NH(CH₂)₃CH₃ |
| 38 | Cl | Cl | NHCH₂CH(CH₃)₂ |
| 39 | Cl | Cl | NHCH(CH₃)CH₂CH₃ |
| 40 | Cl | Cl | NHC(CH₃)₃ |
| 41 | Cl | Cl | NH(CH₂)₄CH₃ |
| 42 | Cl | Cl | NH(CH₂)₂CH(CH₃)₂ |
| 43 | Cl | Cl | NHCH₂C(CH₃)₃ |
| 44 | Cl | Cl | NHC(CH₃)₂CH₂CH₃ |
| 45 | Cl | Cl | NH(CH₂)₅CH₃ |
| 46 | Cl | Cl | NHCH₂CH=CH₂ |
| 47 | Cl | Cl | NHCH₂CH=CHCH₃ |
| 48 | Cl | Cl | NHC₆H₅ |
| 49 | Cl | Cl | NH—(4-CH₃—C₆H₄) |
| 50 | Cl | Cl | NH—(4-Cl—C₆H₄) |
| 51 | Cl | Cl | NH—(2,4-Cl₂—C₆H₃) |
| 52 | Cl | Cl | NH—(4-C(CH₃)₃—C₆H₄) |
| 53 | Cl | Cl | NHCH₂C₆H₅ |
| 54 | Cl | Cl | NHCH₂—(4-CH₃—C₆H₄) |
| 55 | Cl | Cl | NHCH₂—(4-Cl—C₆H₄) |
| 56 | Cl | Cl | NHCH₂—(4-F—C₆H₄) |
| 57 | Cl | Cl | NHCH₂—(2,4-Cl₂—C₆H₃) |
| 58 | Cl | Cl | NHCH₂—(4-C(CH₃)₃—C₆H₄) |
| 59 | Cl | Cl | NHCH₂—(2-CH₃—C₆H₄) |
| 60 | Cl | Cl | NHCH₂—(2-Cl—C₆H₄) |
| 61 | Cl | Cl | NHCH₂—(2-F—C₆H₄) |
| 62 | Cl | Cl | NHCH₂—(3-CH₃—C₆H₄) |
| 63 | Cl | Cl | NHCH₂—(3-Cl—C₆H₄) |
| 64 | Cl | Cl | NHCH₂—(3-F—C₆H₄) |
| 65 | Cl | Cl | O-cyclopropyl |
| 66 | Cl | Cl | O-cyclopentyl |
| 67 | Cl | Cl | O-cyclohexyl |
| 68 | Cl | Cl | NH-cyclopropyl |
| 69 | Cl | Cl | NH-cyclopentyl |
| 70 | Cl | Cl | NH-cyclohexyl |
| 71 | Cl | Cl | CH₃ |
| 72 | Cl | Cl | CH₂CH₃ |
| 73 | Cl | Cl | (CH₂)₂CH₃ |
| 74 | Cl | Cl | CH(CH₃)₂ |
| 75 | Cl | Cl | (CH₂)₃CH₃ |
| 76 | Cl | Cl | CH₂CH(CH₃)₂ |
| 77 | Cl | Cl | CH(CH₃)CH₂CH₃ |
| 78 | Cl | Cl | C(CH₃)₃ |
| 79 | Cl | Cl | (CH₂)₄CH₃ |
| 80 | Cl | Cl | (CH₂)₂CH(CH₃)₂ |
| 81 | Cl | Cl | CH₂C(CH₃)₃ |
| 82 | Cl | Cl | C(CH₃)₂CH₂CH₃ |
| 83 | Cl | Cl | (CH₂)₅CH₃ |
| 84 | Cl | Cl | CH₂CH=CH₂ |
| 85 | Cl | Cl | CH₂CH=CHCH₃ |
| 86 | Cl | Cl | C₆H₅ |
| 87 | Cl | Cl | 4-CH₃—C₆H₄ |
| 88 | Cl | Cl | 4-Cl—C₆H₄ |
| 89 | Cl | Cl | 2,4-Cl₂—C₆H₃ |
| 90 | Cl | Cl | 4-C(CH₃)₃—C₆H₄ |
| 91 | Cl | Cl | CH₂C₆H₅ |
| 92 | Cl | Cl | CH₂—(4-CH₃—C₆H₄) |
| 93 | Cl | Cl | CH₂—(4-Cl—C₆H₄) |
| 94 | Cl | Cl | CH₂—(4-F—C₆H₄) |
| 95 | Cl | Cl | CH₂—(2,4-Cl₂—C₆H₃) |
| 96 | Cl | Cl | CH₂—(4-C(CH₃)₃—C₆H₄) |
| 97 | Cl | Cl | CH₂—(2-CH₃—C₆H₄) |
| 98 | Cl | Cl | CH₂—(2-Cl—C₆H₄) |
| 99 | Cl | Cl | CH₂—(2-F—C₆H₄) |
| 100 | Cl | Cl | CH₂—(3-CH₃—C₆H₄) |
| 101 | Cl | Cl | CH₂—(3-Cl—C₆H₄) |
| 102 | Cl | Cl | CH₂—(3-F—C₆H₄) |

TABLE A-continued

| No. | R² | R³ | R⁴ |
|---|---|---|---|
| 103 | Cl | Cl | cyclopropyl |
| 104 | Cl | Cl | cyclopentyl |
| 105 | Cl | Cl | cyclohexyl |
| 106 | Cl | Cl | 1-CH₃-cyclopropyl |
| 107 | Cl | Cl | 1-CH₃-cyclopentyl |
| 108 | Cl | Cl | 1-CH₃-cyclohexyl |
| 109 | Cl | Cl | 1-Cl-cyclopropyl |
| 110 | Cl | Cl | 1-Cl-cyclopentyl |
| 111 | Cl | Cl | 1-Cl-cyclohexyl |
| 112 | Cl | Cl | 1-OCH₃-cyclopropyl |
| 113 | Cl | Cl | 1-OCH₃-cyclopentyl |
| 114 | Cl | Cl | 1-OCH₃-cyclohexyl |
| 115 | Cl | CH₃ | OCH₃ |
| 116 | Cl | CH₃ | OCH₂CH₃ |
| 117 | Cl | CH₃ | O(CH₂)₂CH₃ |
| 118 | Cl | CH₃ | OCH(CH₃)₂ |
| 119 | Cl | CH₃ | O(CH₂)₃CH₃ |
| 120 | Cl | CH₃ | OCH₂CH(CH₃)₂ |
| 121 | Cl | CH₃ | OCH(CH₃)CH₂CH₃ |
| 122 | Cl | CH₃ | OC(CH₃)₃ |
| 123 | Cl | CH₃ | O(CH₂)₄CH₃ |
| 124 | Cl | CH₃ | O(CH₂)₂CH(CH₃)₂ |
| 125 | Cl | CH₃ | OCH₂C(CH₃)₃ |
| 126 | Cl | CH₃ | OC(CH₃)₂CH₂CH₃ |
| 127 | Cl | CH₃ | O(CH₂)₅CH₃ |
| 128 | Cl | CH₃ | OCH₂CH=CH₂ |
| 129 | Cl | CH₃ | OCH₂CH=CHCH₃ |
| 130 | Cl | CH₃ | OC₆H₅ |
| 131 | Cl | CH₃ | O—(4-CH₃—C₆H₄) |
| 132 | Cl | CH₃ | O—(4-Cl—C₆H₄) |
| 133 | Cl | CH₃ | O—(2,4-Cl₂—C₆H₃) |
| 134 | Cl | CH₃ | O—(4-C(CH₃)₃—C₆H₄) |
| 135 | Cl | CH₃ | OCH₂C₆H₅ |
| 136 | Cl | CH₃ | OCH₂—(4-CH₃—C₆H₄) |
| 137 | Cl | CH₃ | OCH₂—(4-Cl—C₆H₄) |
| 138 | Cl | CH₃ | OCH₂—(4-F—C₆H₄) |
| 139 | Cl | CH₃ | OCH₂—(2,4-Cl₂—C₆H₃) |
| 140 | Cl | CH₃ | OCH₂—(4-C(CH₃)₃—C₆H₄) |
| 141 | Cl | CH₃ | OCH₂—(2-CH₃—C₆H₄) |
| 142 | Cl | CH₃ | OCH₂—(2-Cl—C₆H₄) |
| 143 | Cl | CH₃ | OCH₂—(2-F—C₆H₄) |
| 144 | Cl | CH₃ | OCH₂—(3-CH₃—C₆H₄) |
| 145 | Cl | CH₃ | OCH₂—(3-Cl—C₆H₄) |
| 146 | Cl | CH₃ | OCH₂—(3-F—C₆H₄) |
| 147 | Cl | CH₃ | NHCH₃ |
| 148 | Cl | CH₃ | NHCH₂CH₃ |
| 149 | Cl | CH₃ | NH(CH₂)₂CH₃ |
| 150 | Cl | CH₃ | NHCH(CH₃)₂ |
| 151 | Cl | CH₃ | NH(CH₂)₃CH₃ |
| 152 | Cl | CH₃ | NHCH₂CH(CH₃)₂ |
| 153 | Cl | CH₃ | NHCH(CH₃)CH₂CH₃ |
| 154 | Cl | CH₃ | NHC(CH₃)₃ |
| 155 | Cl | CH₃ | NH(CH₂)₄CH₃ |
| 156 | Cl | CH₃ | NH(CH₂)₂CH(CH₃)₂ |
| 157 | Cl | CH₃ | NHCH₂C(CH₃)₃ |
| 158 | Cl | CH₃ | NHC(CH₃)₂CH₂CH₃ |
| 159 | Cl | CH₃ | NH(CH₂)₅CH₃ |
| 160 | Cl | CH₃ | NHCH₂CH=CH₂ |
| 161 | Cl | CH₃ | NHCH₂CH=CHCH₃ |
| 162 | Cl | CH₃ | NHC₆H₅ |
| 163 | Cl | CH₃ | NH—(4-CH₃—C₆H₄) |
| 164 | Cl | CH₃ | NH—(4-Cl—C₆H₄) |
| 165 | Cl | CH₃ | NH—(2,4-Cl₂—C₆H₃) |
| 166 | Cl | CH₃ | NH—(4-C(CH₃)₃—C₆H₄) |
| 167 | Cl | CH₃ | NHCH₂C₆H₅ |
| 168 | Cl | CH₃ | NHCH₂—(4-CH₃—C₆H₄) |
| 169 | Cl | CH₃ | NHCH₂—(4-Cl—C₆H₄) |
| 170 | Cl | CH₃ | NHCH₂—(4-F—C₆H₄) |
| 171 | Cl | CH₃ | NHCH₂—(2,4-Cl₂—C₆H₃) |
| 172 | Cl | CH₃ | NHCH₂—(4-C(CH₃)₃—C₆H₄) |
| 173 | Cl | CH₃ | NHCH₂—(2-CH₃—C₆H₄) |
| 174 | Cl | CH₃ | NHCH₂—(2-Cl—C₆H₄) |
| 175 | Cl | CH₃ | NHCH₂—(2-F—C₆H₄) |
| 176 | Cl | CH₃ | NHCH₂—(3-CH₃—C₆H₄) |
| 177 | Cl | CH₃ | NHCH₂—(3-Cl—C₆H₄) |
| 178 | Cl | CH₃ | NHCH₂—(3-F—C₆H₄) |
| 179 | Cl | CH₃ | O-cyclopropyl |
| 180 | Cl | CH₃ | O-cyclopentyl |
| 181 | Cl | CH₃ | O-cyclohexyl |
| 182 | Cl | CH₃ | NH-cyclopropyl |
| 183 | Cl | CH₃ | NH-cyclopentyl |
| 184 | Cl | CH₃ | NH-cyclohexyl |
| 185 | Cl | CH₃ | CH₃ |
| 186 | Cl | CH₃ | CH₂CH₃ |
| 187 | Cl | CH₃ | (CH₂)₂CH₃ |
| 188 | Cl | CH₃ | CH(CH₃)₂ |
| 189 | Cl | CH₃ | (CH₂)₃CH₃ |
| 190 | Cl | CH₃ | CH₂CH(CH₃)₂ |
| 191 | Cl | CH₃ | CH(CH₃)CH₂CH₃ |
| 192 | Cl | CH₃ | C(CH₃)₃ |
| 193 | Cl | CH₃ | (CH₂)₄CH₃ |
| 194 | Cl | CH₃ | (CH₂)₂CH(CH₃)₂ |
| 195 | Cl | CH₃ | CH₂C(CH₃)₃ |
| 196 | Cl | CH₃ | C(CH₃)₂CH₂CH₃ |
| 197 | Cl | CH₃ | (CH₂)₅CH₃ |
| 198 | Cl | CH₃ | CH₂CH=CH₂ |
| 199 | Cl | CH₃ | CH₂CH=CHCH₃ |
| 200 | Cl | CH₃ | C₆H₅ |
| 201 | Cl | CH₃ | 4-CH₃—C₆H₄ |
| 202 | Cl | CH₃ | 4-Cl—C₆H₄ |
| 203 | Cl | CH₃ | 2,4-Cl₂—C₆H₃ |
| 204 | Cl | CH₃ | 4-C(CH₃)₃—C₆H₄ |
| 205 | Cl | CH₃ | CH₂C₆H₅ |
| 206 | Cl | CH₃ | CH₂—(4-CH₃—C₆H₄) |
| 207 | Cl | CH₃ | CH₂—(4-Cl—C₆H₄) |
| 208 | Cl | CH₃ | CH₂—(4-F—C₆H₄) |
| 209 | Cl | CH₃ | CH₂—(2,4-Cl₂—C₆H₃) |
| 210 | Cl | CH₃ | CH₂—(4-C(CH₃)₃—C₆H₄) |
| 211 | Cl | CH₃ | CH₂—(2-CH₃—C₆H₄) |
| 212 | Cl | CH₃ | CH₂—(2-Cl—C₆H₄) |
| 213 | Cl | CH₃ | CH₂—(2-F—C₆H₄) |
| 214 | Cl | CH₃ | CH₂—(3-CH₃—C₆H₄) |
| 215 | Cl | CH₃ | CH₂—(3-Cl—C₆H₄) |
| 216 | Cl | CH₃ | CH₂—(3-F—C₆H₄) |
| 217 | Cl | CH₃ | cyclopropyl |
| 218 | Cl | CH₃ | cyclopentyl |
| 219 | Cl | CH₃ | cyclohexyl |
| 220 | Cl | CH₃ | 1-CH₃-cyclopropyl |
| 221 | Cl | CH₃ | 1-CH₃-cyclopentyl |
| 222 | Cl | CH₃ | 1-CH₃-cyclohexyl |
| 223 | Cl | CH₃ | 1-Cl-cyclopropyl |
| 224 | Cl | CH₃ | 1-Cl-cyclopentyl |
| 225 | Cl | CH₃ | 1-Cl-cyclohexyl |
| 226 | Cl | CH₃ | 1-OCH₃-cyclopropyl |
| 227 | Cl | CH₃ | 1-OCH₃-cyclopentyl |
| 228 | Cl | CH₃ | 1-OCH₃-cyclohexyl |
| 229 | CH₃ | Cl | OCH₃ |
| 230 | CH₃ | Cl | OCH₂CH₃ |
| 231 | CH₃ | Cl | O(CH₂)₂CH₃ |
| 232 | CH₃ | Cl | OCH(CH₃)₂ |
| 233 | CH₃ | Cl | O(CH₂)₃CH₃ |
| 234 | CH₃ | Cl | OCH₂CH(CH₃)₂ |
| 235 | CH₃ | Cl | OCH(CH₃)CH₂CH₃ |
| 236 | CH₃ | Cl | OC(CH₃)₃ |
| 237 | CH₃ | Cl | O(CH₂)₄CH₃ |
| 238 | CH₃ | Cl | O(CH₂)₂CH(CH₃)₂ |
| 239 | CH₃ | Cl | OCH₂C(CH₃)₃ |
| 240 | CH₃ | Cl | OC(CH₃)₂CH₂CH₃ |
| 241 | CH₃ | Cl | O(CH₂)₅CH₃ |
| 242 | CH₃ | Cl | OCH₂CH=CH₂ |
| 243 | CH₃ | Cl | OCH₂CH=CHCH₃ |
| 244 | CH₃ | Cl | OC₆H₅ |
| 245 | CH₃ | Cl | O—(4-CH₃—C₆H₄) |
| 246 | CH₃ | Cl | O—(4-Cl—C₆H₄) |
| 247 | CH₃ | Cl | O—(2,4-Cl₂—C₆H₃) |
| 248 | CH₃ | Cl | O—(4-C(CH₃)₃—C₆H₄) |
| 249 | CH₃ | Cl | OCH₂C₆H₅ |
| 250 | CH₃ | Cl | OCH₂—(4-CH₃—C₆H₄) |
| 251 | CH₃ | Cl | OCH₂—(4-Cl—C₆H₄) |
| 252 | CH₃ | Cl | OCH₂—(4-F—C₆H₄) |
| 253 | CH₃ | Cl | OCH₂—(2,4-Cl₂—C₆H₃) |
| 254 | CH₃ | Cl | OCH₂—(4-C(CH₃)₃—C₆H₄) |
| 255 | CH₃ | Cl | OCH₂—(2-CH₃—C₆H₄) |
| 256 | CH₃ | Cl | OCH₂—(2-Cl—C₆H₄) |

TABLE A-continued

| No. | $R^2$ | $R^3$ | $R^4$ |
|---|---|---|---|
| 257 | $CH_3$ | Cl | $OCH_2$—(2-F—$C_6H_4$) |
| 258 | $CH_3$ | Cl | $OCH_2$—(3-$CH_3$—$C_6H_4$) |
| 259 | $CH_3$ | Cl | $OCH_2$—(3-Cl—$C_6H_4$) |
| 260 | $CH_3$ | Cl | $OCH_2$—(3-F—$C_6H_4$) |
| 261 | $CH_3$ | Cl | $NHCH_3$ |
| 262 | $CH_3$ | Cl | $NHCH_2CH_3$ |
| 263 | $CH_3$ | Cl | $NH(CH_2)_2CH_3$ |
| 264 | $CH_3$ | Cl | $NHCH(CH_3)_2$ |
| 265 | $CH_3$ | Cl | $NH(CH_2)_3CH_3$ |
| 266 | $CH_3$ | Cl | $NHCH_2CH(CH_3)_2$ |
| 267 | $CH_3$ | Cl | $NHCH(CH_3)CH_2CH_3$ |
| 268 | $CH_3$ | Cl | $NHC(CH_3)_3$ |
| 269 | $CH_3$ | Cl | $NH(CH_2)_4CH_3$ |
| 270 | $CH_3$ | Cl | $NH(CH_2)_2CH(CH_3)_2$ |
| 271 | $CH_3$ | Cl | $NHCH_2C(CH_3)_3$ |
| 272 | $CH_3$ | Cl | $NHC(CH_3)_2CH_2CH_3$ |
| 273 | $CH_3$ | Cl | $NH(CH_2)_5CH_3$ |
| 274 | $CH_3$ | Cl | $NHCH_2CH=CH_2$ |
| 275 | $CH_3$ | Cl | $NHCH_2CH=CHCH_3$ |
| 276 | $CH_3$ | Cl | $NHC_6H_5$ |
| 277 | $CH_3$ | Cl | NH—(4-$CH_3$—$C_6H_4$) |
| 278 | $CH_3$ | Cl | NH—(4-Cl—$C_6H_4$) |
| 279 | $CH_3$ | Cl | NH—(2,4-$Cl_2$—$C_6H_3$) |
| 280 | $CH_3$ | Cl | NH—(4-C($CH_3$)$_3$—$C_6H_4$) |
| 281 | $CH_3$ | Cl | $NHCH_2C_6H_5$ |
| 282 | $CH_3$ | Cl | $NHCH_2$—(4-$CH_3$—$C_6H_4$) |
| 283 | $CH_3$ | Cl | $NHCH_2$—(4-Cl—$C_6H_4$) |
| 284 | $CH_3$ | Cl | $NHCH_2$—(4-F—$C_6H_4$) |
| 285 | $CH_3$ | Cl | $NHCH_2$—(2,4-$Cl_2$—$C_6H_3$) |
| 286 | $CH_3$ | Cl | $NHCH_2$—(4-C($CH_3$)$_3$—$C_6H_4$) |
| 287 | $CH_3$ | Cl | $NHCH_2$—(2-$CH_3$—$C_6H_4$) |
| 288 | $CH_3$ | Cl | $NHCH_2$—(2-Cl—$C_6H_4$) |
| 289 | $CH_3$ | Cl | $NHCH_2$—(2-F—$C_6H_4$) |
| 290 | $CH_3$ | Cl | $NHCH_2$—(3-$CH_3$—$C_6H_4$) |
| 291 | $CH_3$ | Cl | $NHCH_2$—(3-Cl—$C_6H_4$) |
| 292 | $CH_3$ | Cl | $NHCH_2$—(3-F—$C_6H_4$) |
| 293 | $CH_3$ | Cl | O-cyclopropyl |
| 294 | $CH_3$ | Cl | O-cyclopentyl |
| 295 | $CH_3$ | Cl | O-cyclohexyl |
| 296 | $CH_3$ | Cl | NH-cyclopropyl |
| 297 | $CH_3$ | Cl | NH-cyclopentyl |
| 298 | $CH_3$ | Cl | NH-cyclohexyl |
| 299 | $CH_3$ | Cl | $CH_3$ |
| 300 | $CH_3$ | Cl | $CH_2CH_3$ |
| 301 | $CH_3$ | Cl | $(CH_2)_2CH_3$ |
| 302 | $CH_3$ | Cl | $CH(CH_3)_2$ |
| 303 | $CH_3$ | Cl | $(CH_2)_3CH_3$ |
| 304 | $CH_3$ | Cl | $CH_2CH(CH_3)_2$ |
| 305 | $CH_3$ | Cl | $CH(CH_3)CH_2CH_3$ |
| 306 | $CH_3$ | Cl | $C(CH_3)_3$ |
| 307 | $CH_3$ | Cl | $(CH_2)_4CH_3$ |
| 308 | $CH_3$ | Cl | $(CH_2)_2CH(CH_3)_2$ |
| 309 | $CH_3$ | Cl | $CH_2C(CH_3)_3$ |
| 310 | $CH_3$ | Cl | $C(CH_3)_2CH_2CH_3$ |
| 311 | $CH_3$ | Cl | $(CH_2)_5CH_3$ |
| 312 | $CH_3$ | Cl | $CH_2CH=CH_2$ |
| 313 | $CH_3$ | Cl | $CH_2CH=CHCH_3$ |
| 314 | $CH_3$ | Cl | $C_6H_5$ |
| 315 | $CH_3$ | Cl | 4-$CH_3$—$C_6H_4$ |
| 316 | $CH_3$ | Cl | 4-Cl—$C_6H_4$ |
| 317 | $CH_3$ | Cl | 2,4-$Cl_2$—$C_6H_3$ |
| 318 | $CH_3$ | Cl | 4-C($CH_3$)$_3$—$C_6H_4$ |
| 319 | $CH_3$ | Cl | $CH_2C_6H_5$ |
| 320 | $CH_3$ | Cl | $CH_2$—(4-$CH_3$—$C_6H_4$) |
| 321 | $CH_3$ | Cl | $CH_2$—(4-Cl—$C_6H_4$) |
| 322 | $CH_3$ | Cl | $CH_2$—(4-F—$C_6H_4$) |
| 323 | $CH_3$ | Cl | $CH_2$—(2,4-$Cl_2$—$C_6H_3$) |
| 324 | $CH_3$ | Cl | $CH_2$—(4-C($CH_3$)$_3$—$C_6H_4$) |
| 325 | $CH_3$ | Cl | $CH_2$—(2-$CH_3$—$C_6H_4$) |
| 326 | $CH_3$ | Cl | $CH_2$—(2-Cl—$C_6H_4$) |
| 327 | $CH_3$ | Cl | $CH_2$—(2-F—$C_6H_4$) |
| 328 | $CH_3$ | Cl | $CH_2$—(3-$CH_3$—$C_6H_4$) |
| 329 | $CH_3$ | Cl | $CH_2$—(3-Cl—$C_6H_4$) |
| 330 | $CH_3$ | Cl | $CH_2$—(3-F—$C_6H_4$) |
| 331 | $CH_3$ | Cl | cyclopropyl |
| 332 | $CH_3$ | Cl | cyclopentyl |
| 333 | $CH_3$ | Cl | cyclohexyl |
| 334 | $CH_3$ | Cl | 1-$CH_3$-cyclopropyl |
| 335 | $CH_3$ | Cl | 1-$CH_3$-cyclopentyl |
| 336 | $CH_3$ | Cl | 1-$CH_3$-cyclohexyl |
| 337 | $CH_3$ | Cl | 1-Cl-cyclopropyl |
| 338 | $CH_3$ | Cl | 1-Cl-cyclopentyl |
| 339 | $CH_3$ | Cl | 1-Cl-cyclohexyl |
| 340 | $CH_3$ | Cl | 1-$OCH_3$-cyclopropyl |
| 341 | $CH_3$ | Cl | 1-$OCH_3$-cyclopentyl |
| 342 | $CH_3$ | Cl | 1-$OCH_3$-cyclohexyl |
| 343 | $CH_3$ | F | $OCH_3$ |
| 344 | $CH_3$ | F | $OCH_2CH_3$ |
| 345 | $CH_3$ | F | $O(CH_2)_2CH_3$ |
| 346 | $CH_3$ | F | $OCH(CH_3)_2$ |
| 347 | $CH_3$ | F | $O(CH_2)_3CH_3$ |
| 348 | $CH_3$ | F | $OCH_2CH(CH_3)_2$ |
| 349 | $CH_3$ | F | $OCH(CH_3)CH_2CH_3$ |
| 350 | $CH_3$ | F | $OC(CH_3)_3$ |
| 351 | $CH_3$ | F | $O(CH_2)_4CH_3$ |
| 352 | $CH_3$ | F | $O(CH_2)_2CH(CH_3)_2$ |
| 353 | $CH_3$ | F | $OCH_2C(CH_3)_3$ |
| 354 | $CH_3$ | F | $OC(CH_3)_2CH_2CH_3$ |
| 355 | $CH_3$ | F | $O(CH_2)_5CH_3$ |
| 356 | $CH_3$ | F | $OCH_2CH=CH_2$ |
| 357 | $CH_3$ | F | $OCH_2CH=CHCH_3$ |
| 358 | $CH_3$ | F | $OC_6H_5$ |
| 359 | $CH_3$ | F | $NHCH_3$ |
| 360 | $CH_3$ | F | $NHCH_2CH_3$ |
| 361 | $CH_3$ | F | $NH(CH_2)_2CH_3$ |
| 362 | $CH_3$ | F | $NHCH(CH_3)_2$ |
| 363 | $CH_3$ | F | $NH(CH_2)_3CH_3$ |
| 364 | $CH_3$ | F | $NHCH_2CH(CH_3)_2$ |
| 365 | $CH_3$ | F | $NHCH(CH_3)CH_2CH_3$ |
| 366 | $CH_3$ | F | $NHC(CH_3)_3$ |
| 367 | $CH_3$ | F | $NH(CH_2)_4CH_3$ |
| 368 | $CH_3$ | F | $NH(CH_2)_2CH(CH_3)_2$ |
| 369 | $CH_3$ | F | $NHCH_2C(CH_3)_3$ |
| 370 | $CH_3$ | F | $NHC(CH_3)_2CH_2CH_3$ |
| 371 | $CH_3$ | F | $NH(CH_2)_5CH_3$ |
| 372 | $CH_3$ | F | $NHCH_2CH=CH_2$ |
| 373 | $CH_3$ | F | $NHCH_2CH=CHCH_3$ |
| 374 | $CH_3$ | F | $NHC_6H_5$ |

The novel compounds of the formula I are suitable as fungicides.

The novel compounds, or the compositions containing them, can be applied by spraying, atomizing, dusting, scattering or watering in the form of directly sprayable solutions, powders, suspensions, even high-percentage aqueous, oily or other suspensions or dispersions, emulsions, oil dispersions, pastes, dusting compositions, scattering compositions or granules. The application forms depend on the intended uses; in each case they should if possible ensure the finest dispersion of the active compounds according to the invention.

Normally, the plants are sprayed or dusted with the active compounds or the seeds of the plants are treated with the active compounds.

The formulations are prepared in a known manner, eg. by extending the active compound with solvents and/or carriers, if desired using emulsifiers and dispersants, where if water is used as a diluent other organic solvents can also be used as auxiliary solvents. Suitable auxiliaries for this purpose are mainly: solvents such as aromatics (eg. xylene), chlorinated aromatics (eg. chlorobenzenes), paraffins (eg. petroleum fractions), alcohols (eg. methanol, butanol), ketones (eg. cyclohexanone), amines (eg. ethanolamine, dimethylformamide) and water; carriers such as ground natural minerals (eg. kaolins, aluminas, talc, chalk) and ground synthetic minerals (eg. highly disperse silica, silicates), emulsifiers such as nonionic and anionic emulsifiers (eg. polyoxyethylene fatty alcohol ethers, alkanesulfonates and arylsulfonates) and dispersants such as lignin-sulfite waste liquors and methylcellulose.

Suitable surface-active substances are the alkali metal, alkaline earth metal and ammonium salts of aromatic sulfonic acids, eg. lignosulfonic, phenolsulfonic, naphthalenesulfonic and dibutylnaphthalenesulfonic acid, and also of fatty acids, alkyl- and alkylarylsulfonates, alkyl-, lauryl ether and fatty alcohol sulfates, as well as salts of sulfated hexa-, hepta- and octade-canols, and also of fatty alcohol glycol ethers, condensation products of sulfonated naphthalene and its derivatives with formaldehyde, condensation products of naphthalene or of the naphthalenesulfonic acids with phenol and formaldehyde, polyoxyethylene octylphenol ether, ethoxylated isooctyl-, octyl- or nonylphenol, alkylphenol or tributylphenylpolyglycol ethers, alkylaryl polyether alcohols, isotridecyl alcohol, fatty alcohol ethylene oxide condensates, ethoxylated castor oil, polyoxyethylene or polyoxypropylenealkyl ethers, lauryl alcohol polyglycol ether acetate, sorbitol esters, lignin-sulfite waste liquors or methylcellulose.

Powder, scattering and dusting compositions can be prepared by mixing or joint grinding of the active substances with a solid carrier.

Granules, eg. coated, impregnated and homogeneous granules, can be prepared by binding the active compounds to solid carriers. Solid carriers are mineral earths such as silica gel, silicic acids, silicates, talc, kaolin, limestone, lime, chalk, bole, loess, clay, dolomite, diatomaceous earth, calcium sulfate and magnesium sulfate, magnesium oxide, ground synthetic materials, fertilizers, such as ammonium sulfate, ammonium phosphate, ammonium nitrate, ureas and vegetable products, such as cereal flour, tree bark meal, wood meal and nutshell meal, cellulose powder or other solid carriers.

Examples of such preparations are:

I a solution of 90 parts by weight of the compound No. I.003 and 10 parts by weight, of N-methyl-α-pyrrolidone, which is suitable for application in the form of very small drops;

II. a mixture of 20 parts by weight of the compound No. I.007, 80 parts by weight of xylene, 10 parts by weight of the addition product of from 8 to 10 mol of ethylene oxide to 1 mol of oleic acid N-monoethanolamide, 5 parts by weight of calcium salt of dodecylbenzenesulfonic acid, 5 parts by weight of the addition product of 40 mol of ethylene oxide to 1 mol of castor oil; a dispersion is obtained by finely dispersing the solution in water.

III. an aqueous dispersion of 20 parts by weight of compound No. I.012, 40 parts by weight of cyclohexanone, 30 parts by weight of isobutanol, 20 parts by weight of the addition product of 40 mol of ethylene oxide to 1 mol of castor oil;

IV. an aqueous dispersion of 20 parts by weight of the compound No. I.001, 25 parts by weight of cyclohexanol, 65 parts by weight of a petroleum fraction of boiling point from 210 to 280° C., and 10 parts by weight of the addition product of 40 mol of ethylene oxide to 1 mol of castor oil;

V. a mixture, ground in a hammer mill, of 80 parts by weight of the compound No. I.011, 3 parts by weight of the sodium salt of diisobutylnaphthalene-α-sulfonic acid, 10 parts by weight of the sodium salt of a lignosulfonic acid from a sulfite waste liquor and 7 parts by weight of powdered silica gel; a spray liquor is obtained by finely dispersing the mixture in water;

VI. an intimate mixture of 3 parts by weight of the compound No. I.009 and 97 parts by weight of finely divided kaolin; this dusting composition contains 3% by weight of active compound;

VII. an intimate mixture of 30 parts by weight of the compound No. I.002, 92 parts by weight of powdered silica gel and 8 parts by weight of liquid paraffin which has been sprayed onto the surface of this silica gel; this preparation gives the active compound a good adhesion;

VIII. a stable aqueous dispersion of 40 parts by weight of the compound No. I.005, 10 parts by weight of the sodium salt of a phenolsulfonic acid/urea/formaldehyde condensate, 2 parts by weight of silica gel and 48 parts by weight of water, which can be further diluted;

IX. a stable oily dispersion of 20 parts by weight of the compound No. I.010, 2 parts by weight of the calcium salt of dodecylbenzenesulfonic acid, 8 parts by weight of fatty alcohol polyglycol ether, 20 parts by weight of the sodium salt of a phenolsulfonic acid/urea/formaldehyde condensate and 68 parts by weight of a paraffinic mineral oil.

The novel compounds I are distinguished by an outstanding activity against a broad spectrum of phytopathogenic fungi, in particular from the class of Ascomycetes and Basidiomycetes. They are systemically active in some cases and can be employed as foliar and soil fungicides.

They are of particular importance for the control of a multiplicity of fungi on various crop plants such as wheat, rye, barley, oats, rice, corn, grass, cotton, soybeans, coffee, sugar cane, grapes, fruit and decorative plants and vegetable plants such as cucumbers, beans and cucurbits, and on the seeds of these plants.

The compounds are applied by treating the fungi or the seeds, plants, materials or the soil to be protected from fungal attack with a fungicidally effective amount of the active compounds.

They are applied before or after the infection of the materials, plants or seeds by the fungi.

The novel compounds are specifically suitable for the control of the following plant diseases:

*Erysiphe graminis* (powdery mildew) in cereals, *Erysiphe cichoracearum* and *Sphaerotheca fuliginea* on cucurbits, *Podosphaera leucotricha* on apples, *Uncinula necator* on vines, *Puccinia* species on cereals, *Rhizoctonia* species on cotton and lawns, *Ustilago* species on cereals and sugar cane, *Venturia inaequalis* (scab) on apples, *Helminthosporium* species on cereals, *Septoria nodorum* on wheat, *Botrytis cinerea* (gray mold) on strawberries, vines, decorative plants and vegetables, *Cercospora arachidicola* on groundnuts, *Pseudocercosporella herpotrichoides* on wheat, barley, *Pyricularia oryzae* on rice, *Phytophthora infestans* on potatoes and tomatoes, *Fusarium* and *Verticillium* species on various plants, *Plasmopara viticola* on vines, *Alternaria* species on vegetables and fruit.

The novel compounds can also be employed in the protection of materials (preservation of wood), eg. against *Paecilomyces variotii*.

The fungicidal compositions in general contain from 0.1 to 95, preferably from 0.5 to 90, % by weight of active compound Depending on the type of effect desired, the application rates are from 0.01 to 2.0 kg of active compound per ha.

In seed treatment, amounts of active compound of from 0.001 to 50 g, preferably 0.01 to 10 g, per kilogram of seed are in general needed.

The compositions according to the invention can also be present as fungicides together with other active compounds in the application form, eg. with herbicides, insecticides, growth regulators, fungicides or alternatively with fertilizers.

On mixing with fungicides, in many cases an increase in the fungicidal spectrum of action is obtained here.

The following list of fungicides with which the compounds according to the invention can be applied together is intended to illustrate the combination possibilities, but not restrict them:

sulfur, dithiocarbamates and their derivatives, such as ferric dimethyldithiocarbamate, zinc dimethyldithiocarbamate, zinc ethylenebisdithiocarbamate, manganese ethylenebisdithiocarbamate, manganese zinc ethylenediamine bisdithiocarbamate, tetramethylthiuram disulfide, ammonia complex of zinc N,N-ethylenebisdithiocarbamate, ammonia complex of zinc N,N'-propylenebisdithiocarbamate, zinc N,N'-propylenebisdithiocarbamate, N,N'-polypropylenebis(thiocarbamoyl) disulfide;

nitro derivatives, such as dinitro(1-methylheptyl)phenyl crotonate, 2-sec-butyl-4,6-dinitrophenyl 3,3-dimethylacrylate, 2-sec-butyl-4,6-dinitrophenyl isopropyl carbonate, diisopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonylaminobenzimidazole, 2-(fur-2-yl)benzimidazole, 2-(thiazol-4-yl)benzimidazole, N-(1,1,2,2-tetrachloroethylthio)tetrahydrophthalimide, N-trichloromethylthiotetrahydrophthalimide, N-trichloromethylthiophthalimide;

N-dichlorofluoromethylthio-N',N'-dimethyl-N-phenylsulfamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, 2-thiopyridine-1-oxide, 8-hydroxyquinoline or its copper salt, 2,3-dihydro-5-carboxanilido-6-methyl-1,4-oxathiin, 2,3-dihydro- 5-carboxanilido-6-methyl-1,4-oxathiin-4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diyl-bis(1-(2,2,2-trichloroethyl))formamide, 1-(3,4-dichloroanilino)-1-formylamino-2,2,2-trichloroethane, 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-ylethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, α-[2-(4-chlorophenyl)ethyl]-α-(1,1-dimethylethyl)-1H-1,2,4-triazol-1-ethanol, 1-(3-(2-chlorophenyl)-1-(4-fluorophenyl)oxiran-2-ylmethyl]-1H-1,2,4-triazole, and also various fungicides, such as dodecylguanidine acetate, 3-[3-(3,5-dimethyl-2-oxycyclohexyl)-2-hydroxyethyl]glutarimide, hexachlorobenzene, DL-methyl-N-(2,6-dimethylphenyl)-N-2-furoyl alaninate, DL-N-(2,6-dimethylphenyl)-N-(2'-methoxyacetyl)alanine methyl ester, N-(2,6-dimethylphenyl)-N-chloroacetyl-D,L-2-aminobutyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-[3,5-dichlorophenyl-(5-methyl-5-methoxymethyl]-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dimethylcyclopropane-1,2-dicarboximide, 2-cyano-[N-ethylaminocarbonyl-2-methoximino]acetamide, 1-[2-(2,4-dichlorophenyl)pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine, 1-((bis(4-fluorophenyl)methylsilyl)methyl)-1H-1,2,4-triazole.

The compounds of the formulae I and VI are additionally suitable to control pests from the class of insects, arachnids and nematodes effectively. They can be employed as pesticides in plant protection and in the hygiene, stored products protection and veterinary sector.

The harmful insects include from the order of the butterflies (Lepidoptera), for example, *Adoxophyes orana, Agrotis ypsilon, Agrotis segetum, Alabama argillacea, Anticarsia gemmatalis, Argyresthia conjugella, Autographa gamma, Cacoecia murinana, Capua reticulana, Choristoneura fumiferana, Chilo partellus, Choristoneura occidentalis, Cirphis unipuncta, Cnaphalocrocis medinalis, Crocidolomia binotalis, Cydia pomonella, Dendrolimus pini, Diaphania nitidalis, Diatraea grandiosella, Earias insulana, Elasmopalpus lignosellus, Eupoecilia ambiguella, Feltia subterranea, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera scitella, Lithocolletis blancardella, Lobesia botrana, Loxostege sticticalis, Lymantria dispar, Lymantria monacha, Lyonetia clerkella, Manduca sexta, Malacosoma neustria, Mamestra brassicae, Mocis repanda, Operophthera brumata, Orgyia pseudotsugata, Ostrinia nubilalis, Pandemis heparana, Panolis flammea, Pectinophora gossypiella, Phthorimaea operculella, Phyllocnistis citrella, Pieris brassicae, Plathypena scabra, Platynota stultana, Plutella xylostella, Prays citri, Prays oleae, Prodenia sunia, Prodenia ornithogalli, Pseudoplusia includens, Rhyacionia frustrana, Scrobipalpula absoluta, Sesamia inferens, Sparganothis pilleriana, Spodoptera frugiperda, Spodoptera littoralis, Spodoptera litura, syllepta derogata, Synanthedon myopaeformis, Thaumatopoea pityocampa, Tortrix viridana, Trichoplusia ni, Tryporyza incertulas, Zeiraphera canadensis,* also *Galleria mellonella* and *Sitotroga cerealella, Ephestia cautella, Tineola bisselliella;* from the order of the beetles (Coleoptera), for example, *Agriotes lineatus, Agriotes obscurus, Anthonomus grandis, Anthonomus pomorum, Apion vorax, Atom-*

*aria linearis, Blastophagus piniperda, Cassida nebulosa, Cerotoma trifurcata, Ceuthorhynchus assimilis, Ceuthorhynchus napi, Chaetocnema tibialis, Conoderus vespertinus, Crioceris asparagi, Dendroctonus refipennis, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllopertha horticola, Phyllophaga sp., Phyllotreta chrysocephala, Phyllotreta nemorum, Phyllotreta striolata, Popillia japonica, Psylliodes napi, Scolytus intricatus, Sitona lineatus,* also *Bruchus rufimanus, Bruchus pisorum, Bruchus lentis, Sitophilus granaria, Lasioderma serricorne, Oryzaephilus surinamensis, Rhyzopertha dominica, Sitophilus oryzae, Tribolium castaneum, Trogoderma granarium, Zabrotes subfasciatus;* from the order of the dipterous insects (Diptera), for example, *Anastrepha ludens, Ceratitis capitata, Contarinia sorghicola, Dacus cucurbitae, Dacus oleae, Dasineura brassicae, Delia coarctata, Delia radicum, Hydrellia griseola, Hylemyia platura, Liriomyza sativae, Liriomyza trifolii, Mayetiola destructor, Orseolia oryzae, Oscinella frit, Pegomya hyoscyami, Phorbia antiqua, Phorbia brassicae, Phorbia coarctata, Rhagoletis cerasi, Rhagoletis pomonella, Tipula oleracea, Tipula paludosa,* also *Aedes aegypti, Aedes vexans, Anopheles maculipennis, Chrysomya bezziana, Chrysomya hominivorax, Chrysomya macellaria, Cordylobia anthropophaga, Culex pipiens, Fannia canicularis, Gasterophilus intestinalis, Glossina morsitans, Haematobia irritans, Haplodiplosis equestris, Hypoderma lineata, Lucilia caprina, Lucilia cuprina, Lucilia sericata, Musca domestica, Muscina stabulans, Oestrus ovis, Tabanus bovinus, Simulium damnosum;* from the order of the thrips (Thysanoptera), for example, *Frankliniella fusca, Frankliniella occidentalis, Frankliniella tritici, Haplothrips tritici, Scirtothrips citri, Thrips oryzae, Thrips palmi, Thrips tabaci;* from the order of the hymenopterous insects (Hymenoptera), for example, *Athalia rosae, Atta cephalotes, Atta sexdens, Atta texana, Hoplocampa minuta, Hoplocampa testudinea, Iridomyrmes humilis, Iridomyrmex purpureus, Monomorium pharaonis, Solenopsis geminata, Solenopsis invicta, Solenopsis richteri;* from the order of the bed bugs (Heteroptera), for example, *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus hesperus, Lygus lineolaris, Lygus pratensis, Nezara viridula, Piesma quadrata, Solubea insularis, Thyanta perditor*; from the order of the plant-sucking insects (Homoptera), for example, *Acyrthosiphon onobrychis, Acyrthosiphon pisum, Adelges laricis, Aonidiella aurantii, Aphidula nasturtii, Aphis fabae, Aphis gossypii, Aphis pomi, Aulacorthum solani, Bemisia tabaci, Brachycaudus cardui, Brevicoryne brassicae, Dalbulus maidis, Dreyfusia nordmannianae, Dreyfusia piceae, Dysaphis radicola, Empoasca fabae, Eriosoma lanigerum, Laodelphax striatella, Macrosiphum avenae, Macrosiphum euphorbiae, Macrosiphon rosae, Megoura viciae, Metopolophium dirhodum, Myzus persicae, Myzus cerasi, Nephotettix cincticeps, Nilaparvata lugens, Perkinsiella saccharicida, Phorodon humuli, Planococcus citri, Psylla mali, Psylla piri, Psylla pyricol, Quadraspidiotus perniciosus, Rhopalosiphum maidis, Saissetia oleae, Schizaphis graminum, Selenaspidus articulatus, Sitobion avenae, Sogatella furcifera, Toxoptera citricida, Trialeurodes abutilonea, Trialeurodes vaporariorum, Viteus vitifolii;* from the order of the termites (Isoptera), for example, *Calotermes flavicollis, Leucotermes flavipes, Macrotermes subhyalinus, Odontotermes formosanus, Reticulitermes lucifugus, Termes natalensis;* from the order of the orthopterous insects (Orthoptera), for example, *Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Schistocerca americana, Schistocerca peregrina, Stauronotus maroccanus, Schistocerca gregaria,* also *Acheta domestica, Blatta orientalis, Blattella germanica, Periplaneta americana;* from the order of the Arachnoidea, for example, phytophagous mites such as *Aculops lycopersicae, Aculops pelekassi, Aculus schlechtendali, Brevipalpus phoenicis, Bryobia praetiosa, Eotetranychus carpini, Eutetranychus banksii, Eriophyes sheldoni, Oligonychus pratensis, Panonychus ulmi, Panonychus citri, Phyllocoptruta oleivora, Polyphagotarsonemus latus, Tarsonemus pallidus, Tetranychus cinnabarinus, Tetranychus kanzawai, Tetranchus pacificus, Tetranychus urticae,* ticks such as *Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Rhipicephalus appendiculatus* and *Rhipicephalus evertsi* and animal-parasitic mites such as *Dermanyssus gallinae, Psoroptes ovis* and *Sarcoptes scabiei*; from the class of the nematodes, for example, root gall nematodes, eg. *Meloidogyne hapla, Meloidogyne incognita, Meloidogyne javanica,* cyst-forming nematodes, eg. *Globodera pallida, Globodera rostochiensis, Heterodera avenae, Heterodera glycines, Heterodera schachtii,* migratory endoparasites and semiendoparasitic nematodes, eg. *Heliocotylenchus multicinctus, Hirschmanniella oryzae, Hoplolaimus spp, Pratylenchus brachyurus, Pratylenchus fallax, Pratylenchus penetrans, Pratylenchus vulnus, Radopholus similis, Rotylenchus reniformis, Scutellonema bradys, Tylenchulus semipenetrans,* stem and leaf nematodes, eg. *Anguina tritici, Aphelenchoides besseyi, Ditylenchus angustus, Ditylenchus dipsaci,* virus vectors, eg. *Longidorus spp, Trichodorus christei, Trichodorus viruliferus, Xiphinema index, Xiphinema mediterraneum.*

The compounds I and VI show a particularly good action against pests from the order of the plant-sucking insects (Homoptera).

The active compound concentrations in the ready-for-application preparations can be varied within substantial ranges.

In general, they are from 0.0001 to 10%, preferably from 0.01 to 1%.

The active compounds can also be used with great success in ultra-low volume processes (ULV), where it is possible to apply formulations containing more than 95% by weight of active compound or even the active compound without additives.

The application rate of active compound for controlling pests under practical and outdoor conditions is from 0.01 to 6.0, preferably from 0.1 to 1.0 kg/ha.

In general, the formulations contain from 0.01 to 95% by weight, preferably from 0.1 to 90% by weight, of the active compound. The active compounds are employed here in a purity of from 90% to 100%, preferably from 95% to 100% (by NMR spectrum).

Oils of various types, herbicides, fungicides, pesticides, bactericides can be added to the active compounds, if appropriate also immediately before application (tank mix). These agents can be admixed to the agents according to the invention in a weight ratio of from 1:10 to 10:1.

The compounds I and VI or the compositions containing them are applied by treating the materials, plants, soils or seeds to be protected with an effective amount of a compound I or VI or of a composition containing them.

Synthesis examples

The procedures for preparing the compounds I and VI shown in the synthesis examples below can be used with modification of the starting compounds for obtaining further representatives of the compounds I. Examples prepared accordingly are given in the following tables with physical data.

1. Preparation of the compounds VI 1.1 O-(4-Amino-2,3-dichlorophenyl) O'-benzyl carbonate 1.9 g (0.062 mol) of 80% sodium hydride were added under $N_2$ to a solution of 10 g (0.056 mol) of 4-amino-2,3-dichlorophenol in 200 ml of DMF and the mixture was subsequently stirred at RT for 30 min. It was then cooled to 0° C. and 9.6 g (0.056 mol) of benzyl chloroformate were added dropwise. After 2 h at RT, 100 ml of water were carefully added dropwise and the mixture was extracted three times with 50 ml of methylene chloride. The combined organic phases were washed twice with water, dried and concentrated. The residue was chromatographed on silica gel using cyclohexane:ethyl acetate=2:1. Yield: 8.6 g (49%)

1.2 O-(4-Amino-2-chloro-3-methylphenyl) O'-methyl carbonate 2.5 g (0.088 mol) of 80% sodium hydride were added under $N_2$ to a solution of 12 g (0.076 mol) of 4-amino-2,3-dichlorophenol in 200 ml of DMF and the mixture was subsequently stirred at RT for 30 min. It was then cooled to 0° C. and 5.3 g (0.056 mol) of methyl chloroformate were added dropwise. After 2 h at RT, 100 ml of water was carefully added dropwise and the mixture was extracted three times using 50 ml of methylene chloride. The combined organic phases were washed twice with water, dried and concentrated. The residue was chromatographed on silica gel using cyclohexane:ethyl acetate=2:1. Yield: [lacuna] (63%).

1.3 O-(4-Amino-2,3-dichlorophenyl) N-methylcarbamate 9.4 g (0.165 mol) of methyl isocyanate were slowly added dropwise to a solution of 20 g (0.112 mol) of 4-amino-2,3-dichlorophenol and 0.2 g (0.0013 mol) of DBU in 130 ml of toluene. After 1 h at RT, the mixture was added to 100 ml of n-hexane, and the precipitate was filtered off with suction and washed with diisopropyl ether. Yield: 16.2 g (61.6%)

TABLE

Compounds of the general formula VI $$R^4-\overset{O}{\underset{\|}{C}}-O-\text{[phenyl with } R^3, R^2, NH_2\text{]} \quad VI$$

| No. | $R^3$ | $R^2$ | $R^4$ | Physical data [$^1$H-NMR] |
|---|---|---|---|---|
| VI.01 | Cl | Cl | $OCH_3$ | 3.84(s, 3H); 5.71 (s, 2H); 6.79(d, 1H); 7.12 (d, 1H) |
| VI.02 | Cl | Cl | $OCH(CH_3)_2$ | 1.31(d, 6H); 4.87(m, 1H); 5.71(s, 2H); 6.79(d, 1H); 7.08(d, 1H) |
| VI.03 | Cl | Cl | $O(CH_2)_3CH_3$ | 0.91(t, 3H); 1.37(m, 2H); 1.64(m, 2H); 4.2(t, 2H); 5.7(s, 2H); 6.8(d, 1H); 7.1(d, 1H) |
| VI.04 | Cl | Cl | $OCH_2CH(CH_3)_2$ | 0.93(d, 6H); 1.97(m, 1H); 4.00(d, 2H); 5.72(s, 2H); 6.76(d, 1H); 7.12(d, 1H) |
| VI.05 | Cl | Cl | $OCH_2CH=CH_2$ | 4.73(dd, 2H); 5.34(m, 2H); 5.73(s, 2H); 6.0(m, 1H); 6.79(d, 2H); 7.12 (d, 1H) |
| VI.06 | Cl | Cl | $OCH_2C_6H_5$ | 5.31(s, 2H); 5.71(s, 2H); 6.79(d, 1H); 7.12(d, 1H); 7.4(m, 5H) |
| VI.07 | Cl | Cl | $NHCH_3$ | 2.65(d, 3H); 5.56(s, 2H); 6.63(d, 1H); 6.95(d, 1H) |
| VI.08 | Cl | $CH_3$ | $OCH_3$ | 2.12(s, 3H); 3.81(s, 3H); 5.21(s, 2H); 6.59(d, 1H); 6.92(d, 1H) |
| VI.09 | Cl | $CH_3$ | $OCH_2CH(CH_3)_2$ | 0.89(d, 6H); 2.14(s, 3H); 3.99(d, 2H); 5.2(d, 2H); 6.6(d, 1H); 6.9(d, 1H) |
| VI.10 | Cl | $CH_3$ | $OCH_2CH=CH_2$ | 2.13(s, 3H); 4.7(dd, 2H); 5.2(d, 2H); 5.3(m, 2H); 5.9(m, 1H); 6.6(d, 1H); 6.9(d, 1H) |
| VI.11 | Cl | $CH_3$ | $OCH_2C_6H_5$ | 2.12(s, 3H); 5.23(s, 2H); 5.26(s, 2H); 6.57(d, 1H); 6.9(d, 1H); 7.4(m, 5H) |
| VI.12 | $CH_3$ | Cl | $NHCH_3$ | 1.2(s, 3H); 2.63(d, 3H); 5.08(s, 2H); 6.57(d, 1H); 6.78(d, 1H); 7.57(br, 1H) |

2. Preparation of the active compounds I 2.1 O-(4-N-Pivaloylamino-2,3-dichlorophenyl) O'-benzyl carbonate 0.6 g (0.0059 mol) of triethylamine and then 0.71 g (0.0059 mol) of pivaloyl chloride were added at 0° C. to a solution of 1.7 g (0.0054 mol) of O-(4-amino-2,3-dichlorophenyl) O'-benzyl carbonate in 80 ml of THF. The mixture was stirred overnight at RT and then added to ice-cooled 10% strength hydrochloric acid. After extracting three times with 20 ml of methylene chloride in each case, the combined organic phases were dried and concentrated. The residue which remained was stirred with cyclohexane and filtered off with suction. 1.53 g (72%) of the title compound remained (m.p.: 64° C.).

2.2 O-(4-N-Pivaloylamino-2-chloro-3-methylphenyl) O'-methyl carbonate 1 g (0.0102 mol) of triethylamine and then 1.2 g (0.0102 mol) of pivaloyl chloride were added at 0° C. to a solution of 2 g (0.0093 mol) of O-(4-amino-3-chloro-2-methylphenyl) O'-methyl carbonate in 80 ml of THF. The mixture was stirred overnight at RT and then added to ice-cooled 10% strength hydrochloric acid. After extracting three times with 20 ml of methylene chloride in each case, the combined organic phases were dried and concentrated. The residue which remained was stirred with cyclohexane and filtered off with suction. 1.45 g (52%) of the title compound remained (m.p.: 138° C.).

2.3 O-(4-N-Pivaloylamino-2,3-dichlorophenyl) N-methylcarbamate 0.93 g (0.0092 mol) of triethylamine and then 1.1 g (0.0092 mol) of pivaloyl chloride were added at 0° C. to a solution of 2 g (0.0085 mol) of O-(4-amino-2,3-dichlorophenyl) N-methylcarbamate in 80 ml of THF. The mixture was stirred overnight at RT and then added to ice-cooled 10% strength hydrochloric acid. After extracting three times with 20 ml of methylene chloride in each case, the combined organic phases were washed successively with sodium hydrogencarbonate and water, dried and concentrated. The residue which remained was stirred with cyclohexane and filtered off with suction. 1.7 g (62.7%) of the title compound remained (m.p.: 147°).

TABLE

Compounds of the general formula I $$R-C(CH_3)_2-\underset{\underset{O}{\|}}{C}-NH-\text{[phenyl with }R^2, R^3\text{]}-O-\underset{\underset{O}{\|}}{C}-R^4$$

| No. | R | R³ | R² | R⁴ | M.p. [°C.] |
|---|---|---|---|---|---|
| I.001 | CH₃ | Cl | Cl | OCH₃ | 87 |
| I.002 | CH₃ | Cl | Cl | O(CH₂)₂CH₃ | 122 |
| I.003 | CH₃ | Cl | Cl | O(CH₂)₃CH₃ | 90 |
| I.004 | CH₃ | Cl | Cl | OCH₂CH(CH₃)₂ | 106 |
| I.005 | CH₃ | Cl | Cl | OCH₂CH=CH₂ | 98 |
| I.006 | CH₃ | Cl | Cl | OCH₂C₆H₅ | 64 |
| I.007 | CH₃ | Cl | CH₃ | OCH₃ | 138 |
| I.008 | CH₃ | Cl | CH₃ | OCH(CH₃)₂ | 202 |
| I.009 | CH₃ | Cl | CH₃ | O(CH₂)₃CH₃ | 140 |
| I.010 | CH₃ | Cl | CH₃ | OCH₂CH=CH₂ | 144 |
| I.011 | CH₃ | Cl | CH₃ | OCH₂C₆H₅ | 135 |
| I.012 | CH₃ | Cl | CH₃ | O(CH₂)₂CH(CH₃)₂ | 154 |
| I.013 | 4-Cl-C₆H₄-CH₂- | Cl | Cl | OCH₂CH(CH₃)₂ | 104 |
| I.014 | 4-CH₃-C₆H₄-CH₂- | Cl | Cl | OCH₂CH(CH₃)₂ | 88 |
| I.015 | 4-Cl-C₆H₄-CH₂- | Cl | Cl | NHCH₃ | 144 |
| I.016 | 4-CH₃-C₆H₄-CH₂- | Cl | Cl | NHCH₃ | 130 |
| I.017 | 4-Cl-C₆H₄-CH₂- | F | CH₃ | OCH₂CH(CH₃)₂ | 76 |
| I.018 | 4-CH₃-C₆H₄-CH₂- | F | CH₃ | OCH₂CH(CH₃)₂ | 85 |
| I.019 | 4-CH₃-C₆H₄-CH₂- | F | CH₃ | OCH₂C₆H₅ | 60 |
| I.020 | 4-Cl-C₆H₄-CH₂- | F | CH₃ | OCH₂C₆H₅ | 109 |

TABLE-continued

Compounds of the general formula I $$R-C(CH_3)_2-C(O)-NH-\text{(aryl with } R^2, R^3\text{)}-O-C(O)-R^4$$

| No. | R | R³ | R² | R⁴ | M.p. [°C.] |
|---|---|---|---|---|---|
| I.021 | 4-CH₃-C₆H₄-CH₂ | Cl | Cl | OCH₂C₆H₅ | 65 |
| I.022 | 4-Cl-C₆H₄-CH₂ | Cl | Cl | OCH₂C₆H₅ | 88 |
| I.023 | CH₂Cl | F | CH₃ | OCH₂—C₆H₅ | 110–113 |
| I.024 | CH₂Cl | Cl | Cl | OCH(CH₃)C₂H₅ | 114–115 |
| I.025 | CH₂Br | Cl | Cl | OCH(CH₃)C₂H₅ | 113–115 |
| I.026 | CH₂CH₃ | Cl | Cl | OCH(CH₃)C₂H₅ | 124–125 |
| I.027 | Cl | Cl | Cl | OCH(CH₃)C₂H₅ | Oil |
| I.028 | CH₂CH₂CH₃ | Cl | Cl | OCH(CH₃)C₂H₅ | Oil |
| I.029 | CH₃ | Cl | Cl | OCH(CH₃)C₂H₅ | 121–122 |
| I.030 | CH₃ | Cl | CH₃ | NHCH₃ | Oil |
| I.031 | Cl | Cl | CH₃ | NHCH₃ | 181–183 |
| I.032 | CH₂CH₃ | Cl | CH₃ | NHCH₃ | 185 |
| I.033 | CH₂Br | Cl | CH₃ | NHCH₃ | 175 |
| I.034 | CH₂CH₂CH₃ | Cl | CH₃ | NHCH₃ | 166 |
| I.035 | Cl | Cl | CH₃ | OCH₂C₆H₅ | 94–96 |
| I.036 | CH₂CH₃ | Cl | CH₃ | OCH₂C₆H₅ | 103–105 |
| I.037 | CH₂Cl | Cl | CH₃ | OCH₂C₆H₅ | 139–145 |
| I.038 | CH₂Cl | F | CH₃ | OCH₃ | 95 |
| I.039 | CH₂Br | F | CH₃ | OCH₃ | 198 |
| I.040 | CH₂CH₂CH₃ | F | CH₃ | OCH₃ | 73 |
| I.041 | CH₃ | F | CH₃ | OCH₃ | 95 |
| I.042 | CH₂Cl | F | CH₃ | OCH₂CH(CH₃)₂ | 147 |
| I.043 | CH₂CH₃ | F | CH₃ | OCH₂CH(CH₃)₂ | 135–140 |
| I.044 | CH₂Br | F | CH₃ | OCH₂CH(CH₃)₂ | 138 |
| I.045 | Cl | F | CH₃ | OCH₂CH(CH₃)₂ | 110 |
| I.046 | CH₂CH₂CH₃ | F | CH₃ | OCH₂CH(CH₃)₂ | 106–108 |
| I.047 | CH₃ | F | CH₃ | OCH₂CH(CH₃)₂ | 146 |
| I.048 | CH₂Br | F | CH₃ | OCH₂—C₆H₅ | 113–116 |
| I.049 | CH₂CH₂CH₃ | F | CH₃ | OCH₂—C₆H₅ | 59–61 |
| I.050 | CH₃ | F | CH₃ | OCH₂—C₆H₅ | 106–110 |
| I.051 | CH₂Cl | Cl | Cl | NHCH₃ | 123–124 |
| I.052 | CH₂Br | Cl | Cl | NHCH₃ | 128–130 |
| I.053 | CH₂CH₂CH₃ | Cl | Cl | NHCH₃ | 116 |
| I.054 | CH₂CH₃ | Cl | Cl | NHCH₃ | 122–124 |
| I.055 | Cl | Cl | Cl | NHCH₃ | 124–126 |
| I.056 | CH₂Br | Cl | Cl | OCH₂CH(CH₃)₂ | 92–94 |
| I.057 | CH₂Cl | Cl | Cl | OCH₂CH(CH₃)₂ | 102–104 |
| I.058 | CH₂CH₂CH₃ | Cl | Cl | OCH₂CH(CH₃)₂ | 50 |
| I.059 | CH₂CH₃ | Cl | Cl | OCH₂CH(CH₃)₂ | 82–84 |
| I.060 | Cl | Cl | Cl | OCH₂CH(CH₃)₂ | 58–60 |
| I.061 | CH₂Cl | Cl | Cl | OCH₂C₆H₅ | 79–81 |
| I.062 | CH₂Br | Cl | Cl | OCH₂C₆H₅ | 87–89 |
| I.063 | CH₂CH₂CH₃ | Cl | Cl | OCH₂C₆H₅ | 66–68 |
| I.064 | CH₂CH₃ | Cl | Cl | OCH₂C₆H₅ | Oil |
| I.065 | Cl | Cl | Cl | OCH₂C₆H₅ | Oil |
| I.066 | CH₂Cl | Cl | Cl | OCH₃ | 101–102 |
| I.067 | CH₂Br | Cl | Cl | OCH₃ | 105–108 |
| I.068 | CH₂CH₂CH₃ | Cl | Cl | OCH₃ | 78–80 |
| I.069 | CH₂CH₃ | Cl | Cl | OCH₃ | 80–82 |
| I.070 | Cl | Cl | Cl | OCH₃ | Oil |
| I.071 | CH₂Br | Cl | CH₃ | OCH₂—C₆H₅ | 125 |
| I.072 | CH₂CH₂CH₃ | Cl | CH₃ | OCH₂—C₆H₅ | 97–99 |
| I.073 | Cl | Cl | CH₃ | OCH₂CH(CH₃)₂ | 117 |
| I.074 | CH₂CH₃ | Cl | CH₃ | OCH₂CH(CH₃)₂ | 150 |
| I.075 | CH₂Cl | Cl | CH₃ | OCH₂CH(CH₃)₂ | 151 |
| I.076 | CH₂Br | Cl | CH₃ | OCH₂CH(CH₃)₂ | 144 |
| I.077 | CH₂CH₂CH₃ | Cl | CH₃ | OCH₂CH(CH₃)₂ | 110 |
| I.078 | CH₃ | Cl | Cl | NHCH₂C(CH₃)₂Cl | Oil |
| I.079 | CH₃ | Cl | Cl | NHCH₂CH₃ | Oil |

TABLE-continued

Compounds of the general formula I

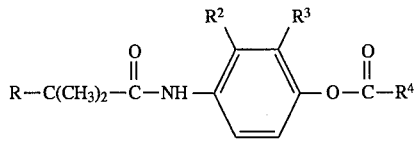

| No. | R | R³ | R² | R⁴ | M.p. [°C.] |
|---|---|---|---|---|---|
| I.080 | $CH_3$ | Cl | Cl | $NHCH_2CH_2CH_3$ | Oil |
| I.081 | $CH_2Cl$ | Cl | Cl | $OC_6H_5$ | 118 |
| I.082 | $CH_3$ | Cl | Cl | $OC_6H_5$ | 106–108 |
| I.083 | $CH_3$ | Cl | Cl | $NH-CH_2-C_6H_5$ | 124 |
| I.084 | $OCH_3$ | Cl | Cl | $OCH_3$ | Oil |
| I.085 | $OCH_3$ | Cl | Cl | $OCH_2CH(CH_3)_2$ | Oil |
| I.086 | $OCH_3$ | Cl | Cl | $OCH_2C_6H_5$ | Oil |

Use examples

It was possible to show the fungicidal action of the compounds of the general formula I by the following tests:

The active compounds were prepared as a 20% strength emulsion in a mixture of 70% by weight of cyclohexanol, 20% by weight of Nekanil® LN (Lutensol® AP6, wetting agent having emulsifier and dispersant action based on ethoxylated alkylphenols) and 10% by weight Emulphor® EL (Emulan® EL, emulsifier based on ethoxylated fatty alcohols) and diluted with water according to the concentration desired.

1. Botrytis cinerea

Paprika seedlings of the variety Neusiedler Ideal Elite having 4–5 well-developed leaves were sprayed until dripping wet with an aqueous active compound suspension. After the spray coating had dried on, the plants were sprayed with a conidia suspension of the fungus Botrytis cinerea. After 5 days at 22° C.–24° C. and high atmospheric humidity, the fungal attack on the leaves was assessed.

In this test, the plants treated with 500 ppm of the compounds I.001, I.004, I.005, I.006 and I.007 showed 15% and less attack, while in the case of the untreated plants 65% of the leaf surfaces were attacked.

2. Plasmopara viticola

Leaves of potted vines of the variety Müller-Thurgau were sprayed until dripping wet with an aqueous active compound suspension. After 8 days in the greenhouse, the plants were infected with a zoospore suspension of Plasmopara viticola (vine Peronospora). The plants were then first kept at 24° C. and 100% atmospheric humidity for 48 hours and then at 20° C.–30° C. for 5 days in a greenhouse. The plants were then again kept at 24° C. and 100% atmospheric humidity for 16 hours before assessment of the attack.

In this test, the plants treated with 250 ppm of the compound I.005 showed 5% attack, while in the case of the untreated plants 70% of the leaf undersides were attacked.

3. Insecticidal action

It was possible to show the insecticidal action of the compounds of the general formula I by the following tests:

The active compounds were prepared a) as a 0.1% strength solution in acetone or b) as a 10% strength emulsion in a mixture of 70% by weight of cyclohexanone, 20% by weight of Nekanil® LN (Lutensol® AP6, wetting agent having emulsifier and dispersant action based on ethoxylated alkylphenols) and 10% by weight of Emulphor® EL (Emulan® EL, emulsifier based on ethoxylated fatty alcohols) and diluted with acetone in the case of (a) or with water in the case of (b) according to the desired concentration.

After conclusion of the tests, the lowest concentration at which the compounds still caused an 80–100% inhibition or mortality in comparison with untreated control tests was determined in each case (activity threshold or minimum concentration).

It was possible to show the insecticidal action of the compounds of the general formula VI by the following tests:

The active compound VI.07 was prepared a) as a 0.1% strength solution in acetone or b) as a 10% strength emulsion in a mixture of 70% by weight of cyclohexanone, 20% by weight of Nekanil® LN (Lutensol® AP6, wetting agent having emulsifier and dispersant action based on ethoxylated alkylphenols) and 10% by weight of Emulphor® EL (Emulan® EL, emulsifier based on ethoxylated fatty alcohols) and diluted with acetone in the case of (a) or with water in the case of (b) according to the desired concentration.

α) Contact test in Petri dishes with the green rice leafhopper (Nephotettix cincticeps)

Round filters of diameter 9 cm were treated with 1 cm³ of the active compound formulated as described in (b) and placed in a plastic Petri dish, having projections, of 9.4 cm diameter. 5 adult rice leafhoppers were then inserted and the Petri dish was closed.

When using the active compound in acetone solution as described in (a), the experiment was carried out in glass Petri dishes of diameter 10 cm. The filter was in this case moistened with 1 cm³ of water after evaporating the acetone.

The mortality was determined after 24 hours.

β) Spray test on intact plant with the green rice leafhopper (Nephotettix cincticeps)

Rice plants about 8 cm high in plastic pots of 9 cm diameter were sprayed until dripping wet with an active compound preparation according to (b) in the spray cabin and, after drying off, placed under a plastic cylinder of diameter 13 cm and height 30 cm. 10 adult rice leafhoppers were inserted and the cylinder was closed with gauze.

The mortality was determined after 48 hours.

In both tests, beginning with 400 ppm (0.4 mg) of active compound per batch down to 100 ppm of active compound a 100% mortality was recorded with the rice leafhoppers.

We claim:
1. A p-hydroxyaniline derivative of the formula I

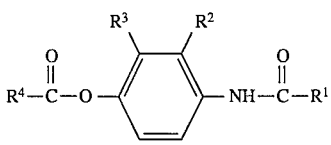

where the substituents have the following meanings:
- $R^1$ is hydrogen, $C_1$–$C_8$-alkyl which can be partly or completely halogenated and/or which can carry one or two of the following radicals: $C_1$–$C_4$-alkoxy, $C_1$–$C_4$-haloalkoxy, $C_1$–$C_4$-alkylthio, $C_3$–$C_7$-cycloalkyl or $C_5$–$C_7$-cycloalkenyl, the cyclic radicals in turn being able to carry one to three halogen atoms, $C_1$–$C_3$-alkyl groups and/or $C_1$–$C_3$-alkoxy groups and aryl, which can be partly or completely halogenated and/or can carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;
- $R^2$ and $R^3$ independently of one another are halogen, $C_1$–$C_4$-alkyl, $C_1$–$C_4$-haloalkyl, $C_1$–$C_4$-alkoxy or $C_1$–$C_4$-haloalkoxy;
- $R^4$ is $C_1$–$C_6$-alkyl or $C_2$–$C_6$-alkenyl, it being possible for these groups to be partly or completely halogenated and/or to carry one of the following radicals: $C_1$–$C_4$-alkoxy, $C_1$–$C_4$-haloalkoxy, $C_1$–$C_4$-alkylthio, $C_3$–$C_7$-cycloalkyl, $C_5$–$C_7$-cycloalkenyl or aryl, the aromatic radicals in turn being able to carry one to three of the following groups: nitro, cyano, halogen, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;
  - $C_3$–$C_7$-cycloalkyl or $C_5$–$C_7$-cycloalkenyl, these groups being able to carry one to three of the following radicals: halogen, $C_1$–$C_4$-alkyl, $C_1$–$C_4$-haloalkyl, $C_1$–$C_4$-alkoxy;
  - aryl, which can be partly or completely halogenated and/or can carry one to three of the following radicals:
    nitro, cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio: or
  - $OR^5$, where
- $R^5$ is $C_1$–$C_6$-alkyl or $C_2$–$C_6$-alkenyl, it being possible for these groups to be partly or completely halogenated and/or to carry one of the following radicals: $C_1$–$C_4$-alkoxy, $C_1$–$C_4$-haloalkoxy, $C_1$–$C_4$-alkylthio, $C_3$–$C_7$-cycloalkyl, $C_5$–$C_7$-cycloalkenyl or aryl, it being possible for the aromatic radicals in turn to carry one to three of the following groups: nitro, cyano, halogen, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio; is $C_3$–$C_6$-cycloalkyl or $C_5$–$C_7$-cycloalkenyl, it being possible for these groups to be partly or completely halogenated and/or to carry one of the following radicals: halogen, $C_1$–$C_4$-alkyl, $C_1$–$C_4$-haloalkyl, $C_1$–$C_4$-alkoxy;
  - or is aryl, which can be partly or completely halogenated and/or can carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

where $R^1$, $R^2$, and $R^4$ are not simultaneously methyl, or its salts.

2. A p-hydroxyaniline of the formula I according to claim 1, wherein
- $R^1$ is —$C(CH_3)_2CH_2Cl$
- $R^2$ and $R^3$ each are Cl, and
- $R^4$ is —$OCH_2CH(CH_3)_2$.

3. A process for preparing the compounds I as claimed in claim 1, which comprises reacting a p-hydroxyaniline of the formula II

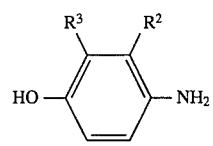

in an inert organic solvent in the presence of a base with a carbonyl derivative of the formula III

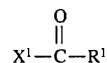

where $X^1$ is halogen or a leaving group which can be used in acylation reactions, to give a carboxamide of the formula IV

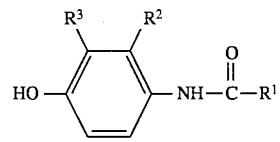

and then converting IV to I by reaction with a carbonyl derivative of the formula Va

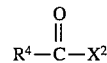

where $X^2$ is halogen or a leaving group which can be used in acylation reactions.

4. A process for preparing the compounds I as claimed in claim 1 which comprises reacting a p-hydroxyaniline of the formula II

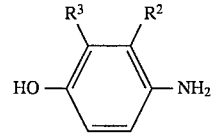

in an inert organic solvent in the presence of a base with a carbonyl derivative of the formula V

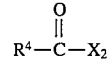

wherein $X^2$ is halogen, to give a compound of the formula VI

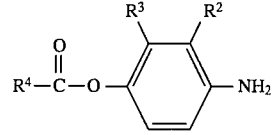

and then converting VI to I by reaction with a carbonyl derivative of the formula III

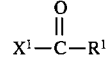

wherein $X^2$ is a halogen or a leaving group which can be used in acylation reactions.

5. A composition suitable for controlling harmful fungi or pests, containing a solid or liquid carrier and a compound of the general formula I as claimed in claim 1.

6. A process for controlling harmful fungi, which comprises treating the harmful fungi, their environment or the plants, surfaces, materials or spaces to be kept free from them with an effective amount of a compound of the general formula I as claimed in claim 1.

* * * * *